United States Patent
Catanese, Jr. et al.

(10) Patent No.: US 12,139,714 B1
(45) Date of Patent: Nov. 12, 2024

(54) P53, P63, AND P73 HOMO-TETRAMERIC COMPOSITIONS

(71) Applicant: TWISTER BIOTECH, LLC, Houston, TX (US)

(72) Inventors: Daniel James Catanese, Jr., Houston, TX (US); Christopher Elbert Coker, Houston, TX (US)

(73) Assignee: TWISTER BIOTECH, LLC, Houston, TX (US)

( * ) Notice: Subject to any disclaimer, the term of this patent is extended or adjusted under 35 U.S.C. 154(b) by 0 days.

(21) Appl. No.: 17/930,526

(22) Filed: Sep. 8, 2022

Related U.S. Application Data

(60) Provisional application No. 63/243,059, filed on Sep. 10, 2021.

(51) Int. Cl.
| | | |
|---|---|---|
| C12N 15/62 | (2006.01) | |
| A61P 35/00 | (2006.01) | |
| A61P 37/02 | (2006.01) | |

(52) U.S. Cl.
CPC .............. *C12N 15/62* (2013.01); *A61P 35/00* (2018.01); *A61P 37/02* (2018.01)

(58) Field of Classification Search
CPC ........... C12N 15/62; A61P 35/00; A61P 37/02
See application file for complete search history.

(56) References Cited

U.S. PATENT DOCUMENTS

| | | | |
|---|---|---|---|
| 5,573,925 A | 11/1996 | Halazonetis | |
| 2002/0068283 A1 | 6/2002 | Boeke et al. | |
| 2016/0347806 A1 | 12/2016 | Lim et al. | |
| 2020/0048716 A1* | 2/2020 | Zechiedrich | ............ A61P 35/00 |

OTHER PUBLICATIONS

Waterman, M. J.; Waterman, J. L.; Halazonetis, T. D. "An engineered four-stranded coiled coil substitutes for the tetramerization domain of wild-type p53 and alleviates transdominant inhibition by tumor-derived p53 mutants." (1996) Cancer Research 56(1), 158-163.

Almazov, V. P.; Morgunkova, A. A.; Kalinin V. N.; Kopnin, B. P.; Prasolov, V. S.; CHUMAKOV, P. M. "Construction of chimeric tumor suppressor p53 resistant to the dominant-negative interaction with p53 mutants." (2002) Mol Biol (Mosk) 36(4):664-71.

Okal, A.; Mossalam, M.; Matissek, K. J.; Dixon, A. S.; MOSS, P. J.; Lim, C. S. "A chimeric p53 evades mutant p53 transdominant inhibition in cancer cells." (2013) Mol Pharm 10(10):3922-33.

Gencel-Augusto J.; Lozano, G. "p53 tetramerization: at the center of the dominant-negative effect of mutant p53" (2020) Genes Dev. 34(17-18):1128-1146.

* cited by examiner

*Primary Examiner* — Elly-Gerald Stoica
(74) *Attorney, Agent, or Firm* — Boulware & Valoir PLLC

(57) ABSTRACT

P63 and p73 (and their genes TP53, TP63, TP73) are truncated at or around the tetramerization domain and fused in frame to a heterologous tetramerization domain from a bacterial gene/protein or viral gene/protein or non-human protein lacking homology to any human proteins. Alternatively, the native tetramerization domain can be excised leaving some 3' sequences. These fusion proteins have the activity of the original protein but are unable to hetero-tetramerize or dimerize or be negatively regulated. Further, since non-human tetramerization sequences with minimal homology to human sequences are used, the fusion proteins will not interact with other tetramerization domains in the cell. Gene therapy treatments can thus be used to treat diseases in which these proteins are implicated, such as cancer, autoimmune, and autoinflammatory diseases.

5 Claims, 23 Drawing Sheets

Specification includes a Sequence Listing.

FIGURE 1. SEQ ID NO. 1: P53 with oligomerization domain in bold

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT EVVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLDGEYFTL QIRGRERFEM FRELNEALEL KDAQAGKEPG
GSRAHSSHLK SKKGQSTSRH KKLMFKTEGP DSD
```

FIGURE 2. SEQ ID NO. 2: P63 with oligomerization domain in bold

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKR**SPDDEL LYLPVRGRET YEMLLKIKES
LELMQYLPQH TIETYRQQQQ QQH**QHLLQKQ TSIQSPSSYG NSSPPLNKMN SMNKLPSVSQ
LINPQQRNAL TPTTIPDGMG ANIPMMGTHM PMAGDMNGLS PTQALPPPLS MPSTSHCTPP
PPYPTDCSIV SFLARLGCSS CLDYFTTQGL TTIYQIEHYS MDDLASLKIP EQFRHAIWKG
ILDHRQLHEF SSPSHLLRTP SSASTVSVGS SETRGERVID AVRFTLRQTI SFPPRDEWND
FNFDMDARRN KQQRIKEEGE
```

FIGURE 3. SEQ ID NO. 3: P73 with oligomerization domain in bold

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV**KKRRHG DEDTYYLQVR
GRENFEILMK LKESLELMEL VPQPLV**DSYR QQQQLLQRPS HLQPPSYGPV LSPMNKVHGG
MNKLPSVNQL VGQPPPHSSA ATPNLGPVGP MLNNHGHAV PANGEMSSSH SAQSMVSGSH
CTPPPPYHAD PSLVSFLTGL GCPNCIEYFT SQGLQSIYHL QNLTIEDLGA LKIPEQYRMT
IWRGLQDLKQ GHDYSTAQQL LRSSNAATIS IGGSGELQRQ RVMEAVHFRV RHTITIPNRG
GPGGGPDEWA DFGFDLPDCK ARKQPIKEEF TEAEIH
```

FIGURE 4. SEQ ID NO. 4: Lac Repressor with tetramerization domain in bold

```
MKPVTLYDVA EYAGVSYQTV SRVVNQASHV SAKTREKVEA AMAELNYIPN RVAQQLAGKQ
SLLIGVATSS LALHAPSQIV AAIKSRADQL GASVVVSMVE RSGVEACKAA VHNLLAQRVS
GLIINYPLDD QDAIAVEAAC TNVPALFLDV SDQTPINSII FSHEDGTRLG VEHLVALGHQ
QIALLAGPLS SVSARLRLAG WHKYLTRNQI QPIAEREGDW SAMSGFQQTM QMLNEGIVPT
AMLVANDQMA LGAMRAITES GLRVGADISV VGYDDTEDSS CYIPPLTTIK QDFRLLGQTS
VDRLLQLSQG QAVKGNQLLP VSLVKRKTTL APNTQTASPR ALADSLMQLA RQVSRLESGQ
```

FIGURE 5. SEQ ID NO. 5: p53CDlac (v1)

```
MEEPQSDPSV EPPLSQETFS DLWKLLPENN VLSPLPSQAM DDLMLSPDDI
EQWFTEDPGP DEAPRMPEAA PPVAPAPAAP TPAAPAPAPS WPLSSSVPSQ
KTYQGSYGFR LGFLHSGTAK SVTCTYSPAL NKMFCQLAKT CPVQLWVDST
PPPGTRVRAM AIYKQSQHMT VVRRCPHHE RCSDSDGLAP PQHLIRVEGN
LRVEYLDDRN TFRHSVVVPY EPPEVGSDCT TIHYNYMCNS SCMGGMNRRP
ILTIITLEDS SGNLLGRNSF EVRVCACPGR DRRTEEENLR KKGEPHHELP
PGSTKRALPN NTSSSPQPKK KPLDTASPR ALADSLMQLA RQVSRLESGQ
```

FIGURE 6. SEQ ID NO. 6: MiniVector encoding CMV-p53CDlac (v1)

```
TTTATACTAACTTGAGCGAAACGGGAAGGGTTTGACATTGATTATTGACTAGTTATTAATAGTAATCA
ATTACGGGGTCATTAGTTCATAGCCCATATATGGAGTTCCGCGTTACATAACTTACGGTAAATGGCCC
GCCTGGCTGACCGCCCAACGACCCCCGCCCATTGACGTCAATAATGACGTATGTTCCCATAGTAACGC
CAATAGGGACTTTCCATTGACGTCAATGGGTGGAGTATTTACGGTAAACTGCCCACTTGGCAGTACAT
CAAGTGTATCATATGCCAAGTACGCCCCCTATTGACGTCAATGACGGTAAATGGCCCGCCTGGCATTA
TGCCCAGTACATGACCTTATGGGACTTTCCTACTTGGCAGTACATCTACGTATTAGTCATCGCTATTA
CCATGGTGATGCGGTTTTGGCAGTACATCAATGGGCGTGGATAGCGGTTTGACTCACGGGGATTTCCA
AGTCTCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATAAGCA
GAGCTCTCTCTGGCTAACTAGAGAACCCACTGCTTACTGGCTTATCGAAATTAATACGACTCACTATA
GGGAGACCCAAGCTTGGTACCATGGAGGAGCCGCAGTCAGATCCTAGCGTCGAGCCCCCTCTGAGTCA
GGAAACATTTTCAGACCTATGGAAACTACTTCCTGAAAACAACGTTCTGTCCCCCTTGCCGTCCCAAG
CAATGGATGATTTGATGCTGTCCCGGACGATATTGAACAATGGTTCACTGAAGACCCAGGTCCAGAT
GAAGCTCCCAGAATGCCAGAGGCTGCTCCCCCGTGGCCCCTGCACCAGCAGCTCCTACACCGGCGGC
CCCTGCACCAGCCCCCTCCTGGCCCTGTCATCTTCTGTCCCTTCCCAGAAAACCTACCAGGGCAGCT
ACGGTTTCCGTCTGGGCTTCTTGCATTCTGGGACAGCCAAGTCTGTGACTTGCACGTACTCCCCTGCC
CTCAACAAGATGTTTTGCCAACTGGCCAAGACCTGCCCTGTGCAGCTGTGGGTTGATTCCACACCCCC
GCCCGGCACCCGCGTCCGCGCCATGGCCATCTACAAGCAGTCACAGCACATGACGGAGGTTGTGAGGC
GCTGCCCCCACCATGAGCGCTGCTCAGATAGCGATGGTCTGGCCCCTCCTCAGCATCTTATCCGAGTG
GAAGGAAATTTGCGTGTGGAGTATTTGGATGACAGAAACACTTTTCGACATAGTGTGGTGGTGCCCTA
TGAGCCGCCTGAGGTTGGCTCTGACTGTACCACCATCCACTACAACTACATGTGTAACAGTTCCTGCA
TGGGCGGCATGAACCGGAGGCCCATCCTCACCATCATCACACTGGAAGACTCCAGTGGTAATCTACTG
GGACGGAACAGCTTTGAGGTGCGTGTTTGTGCCTGTCCTGGGAGAGACCGGCGCACAGAGGAAGAGAA
TCTCCGCAAGAAAGGGGAGCCTCACCACGAGCTGCCCCCAGGGAGCACTAAGCGAGCACTGCCCAACA
ACACCAGCTCCTCTCCCCAGCCAAAGAAGAAACCACTGGATGGAGAATATACCGCCTCTCCCCGCGCG
TTGGCCGATTCATTAATGCAGCTGGCACGACAGGTTTCCCGACTGGAAAGCGGGCAGTAATTCGAGCA
GACATGATAAGATACATTGATGAGTTTGGACAAACCACAACTAGAATGCAGTGAAAAAAATGCTTTAT
TTGTGAAATTTGTGATGCTATTGCTTTATTTGTAACCATTATAAGCTGCAATAAACAAGTTTATCCGC
GCAAGCTTCCTCAGCTCTGTTACAGGTCACTAATACCATCTAAGTAGTTGATTCATAGTGACTGCATA
TGTTGTGTTTTACAGTATTATGTAGTCTGTTTTTTATGCAAAATCTAATTTAATATATTGATATTTAT
ATCATTTTACGTTTCTCGTTCAGCTTT
```

FIGURE 7. SEQ ID NO. 7: p53CDlac (v2)

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLDSPR ALADSLMQLA RQVSRLESGQ
```

FIGURE 8. SEQ ID NO. 8: p53CDlac (v3)

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLDR ALADSLMQLA RQVSRLESGQ
```

FIGURE 9. SEQ ID NO. 9: p53CDlac (v4)

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLDLADSLMQLA RQVSRLESGQ
```

FIGURE 10. SEQ ID NO. 10: p53CDlac (v5)

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLDDSLMQLA RQVSRLESGQ
```

FIGURE 11. SEQ ID NO. 11: p53CDlac (v6)

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLDLMQLA RQVSRLESGQ
```

FIGURE 12. SEQ ID NO. 12: p53CDlac (v7)

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLDQLA RQVSRLESGQ
```

FIGURE 13. SEQ ID NO. 13: p53CDlac (v8)

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLDA RQVSRLESGQ
```

FIGURE 14. SEQ ID NO. 14: p63CDlac (v1)

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKRTASPR ALADSLMQLA RQVSRLESGQ
```

FIGURE 15. SEQ ID NO. 15: p63CDlac (v2)

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKRSPR ALADSLMQLA RQVSRLESGQ
```

FIGURE 16. SEQ ID NO. 16: p63CDlac (v3)

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKRR ALADSLMQLA RQVSRLESGQ
```

FIGURE 17. SEQ ID NO. 17: p63CDlac (v4)

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKRLADSLMQLA RQVSRLESGQ
```

FIGURE 18. SEQ ID NO. 18: p63CDlac (v5)

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKRDSLMQLA RQVSRLESGQ
```

FIGURE 19. SEQ ID NO. 19: p63CDlac (v6)

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKRLMQLA RQVSRLESGQ
```

FIGURE 20. SEQ ID NO. 20: p63CDlac (v7)

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKRQLA RQVSRLESGQ
```

FIGURE 21. SEQ ID NO. 21: p63CDlac (v8)

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKRA RQVSRLESGQ
```

FIGURE 22. SEQ ID NO. 22: p73CDlac (v1)

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV**TASPR ALADSLMQLA
RQVSRLESGQ**
```

FIGURE 23. SEQ ID NO. 23: p73CDlac (v2)

MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV**SPR ALADSLMQLA
RQVSRLESGQ**

FIGURE 24. SEQ ID NO. 24: p73CDlac (v3)

MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV**R ALADSLMQLA
RQVSRLESGQ**

FIGURE 25. SEQ ID NO. 25: p73CDlac (v4)

MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGVLADSLMQLA RQVSRLESGQ

FIGURE 26. SEQ ID NO. 26: p73CDlac (v5)

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGVDSLMQLA RQVSRLESGQ
```

FIGURE 27. SEQ ID NO. 27: p73CDlac (v6)

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGVLMQLA RQVSRLESGQ
```

FIGURE 28. SEQ ID NO. 28: p73CDlac (v7)

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGVQLA RQVSRLESGQ
```

FIGURE 29. SEQ ID NO. 29: p73CDlac (v8)

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGVA RQVSRLESGQ
```

FIGURE 30. SEQ ID No: 30. MatP with tetramerization domain in bold

```
MKYQQLENLE  SGWKWKYLVK  KHREGELITR  YIEASAAQEA  VDVLLSLENE  PVLVNGWIDK
HMNPELVNRM  KQTIRARRKR  HFNAEHQHTR  KKSIDLEFIV  WQRLAGLAQR  RGKTLSETIV
QLIEDAENKE  KYANKMSSLK  QDLQALLGKE
```

FIGURE 31. SEQ ID NO. 31: p53CDmat

```
MEEPQSDPSV  EPPLSQETFS  DLWKLLPENN  VLSPLPSQAM  DDLMLSPDDI  EQWFTEDPGP
DEAPRMPEAA  PPVAPAPAAP  TPAAPAPAPS  WPLSSSVPSQ  KTYQGSYGFR  LGFLHSGTAK
SVTCTYSPAL  NKMFCQLAKT  CPVQLWVDST  PPPGTRVRAM  AIYKQSQHMT  VVRRCPHHE
RCSDSDGLAP  PQHLIRVEGN  LRVEYLDDRN  TFRHSVVVPY  EPPEVGSDCT  TIHYNYMCNS
SCMGGMNRRP  ILTIITLEDS  SGNLLGRNSF  EVRVCACPGR  DRRTEEENLR  KKGEPHHELP
PGSTKRALPN  NTSSSPQPKK  KPLDANKMSSLK  QDLQALLGKE
```

FIGURE 32. SEQ ID NO. 32: p63CDmat

```
MNFETSRCAT  LQYCPDPYIQ  RFVETPAHFS  WKESYYRSTM  SQSTQTNEFL  SPEVFQHIWD
FLEQPICSVQ  PIDLNFVDEP  SEDGATNKIE  ISMDCIRMQD  SDLSDPMWPQ  YTNLGLLNSM
DQQIQNGSSS  TSPYNTDHAQ  NSVTAPSPYA  QPSSTFDALS  PSPAIPSNTD  YPGPHSFDVS
FQQSSTAKSA  TWTYSTELKK  LYCQIAKTCP  IQIKVMTPPP  QGAVIRAMPV  YKKAEHVTEV
VKRCPNHELS  REFNEGQIAP  PSHLIRVEGN  SHAQYVEDPI  TGRQSVLVPY  EPPQVGTEFT
TVLYNFMCNS  SCVGGMNRRP  ILIIVTLETR  DGQVLGRRCF  EARICACPGR  DRKADEDSIR
KQQVSDSTKN  GDGTKRPFRQ  NTHGIQMTSI  KKRANKMSSLK  QDLQALLGKE
```

FIGURE 33. SEQ ID NO. 33: p73CDmat

```
MAQSTATSPD  GGTTFEHLWS  SLEPDSTYFD  LPQSSRGNNE  VVGGTDSSMD  VFHLEGMTTS
VMAQFNLLSS  TMDQMSSRAA  SASPYTPEHA  ASVPTHSPYA  QPSSTFDTMS  PAPVIPSNTD
YPGPHHFEVT  FQQSSTAKSA  TWTYSPLLKK  LYCQIAKTCP  IQIKVSTPPP  PGTAIRAMPV
YKKAEHVTDV  VKRCPNHELG  RDFNEGQSAP  ASHLIRVEGN  NLSQYVDDPV  TGRQSVVVPY
EPPQVGTEFT  TILYNFMCNS  SCVGGMNRRP  ILIIITLEMR  DGQVLGRRSF  EGRICACPGR
DRKADEDHYR  EQQALNESSA  KNGAASKRAF  KQSPPAVPAL  GAGVANKMSSLK  QDLQALLGKE
```

FIGURE 34. SEQ ID No. 34: MutS with tetramerization domain in bold

```
MSAIENFDAH TPMMQQYLRL KAQHPEILLF YRMGDFYELF YDDAKRASQL LDISLTKRGA
SAGEPIPMAG IPYHAVENYL AKLVNQGESV AICEQIGDPA TSKGPVERKV VRIVTPGTIS
DEALLQERQD NLLAAIWQDS KGFGYATLDI SSGRFRLSEP ADRETMAAEL QRTNPAELLY
AEDFAEMSLI EGRRGLRRRP LWEFEIDTAR QQLNLQFGTR DLVGFGVENA PRGLCAAGCL
LQYAKDTQRT TLPHIRSITM EREQDSIIMD AATRRNLEIT QNLAGGAENT LASVLDCTVT
PMGSRMLKRW LHMPVRDTRV LLERQQTIGA LQDFTAGLQP VLRQVGDLER ILARLALRTA
RPRDLARMRH AFQQLPELRA QLETVDSAPV QALREKMGEF AELRDLLERA IIDTPPVLVR
DGGVIASGYN EELDEWRALA DGATDYLERL EVRERERTGL DTLKVGFNAV HGYYIQISRG
QSHLAPINYM RRQTLKNAER YIIPELKEYE DKVLTSKGKA LALEKQLYEE LFDLLLPHLE
ALQQSASALA ELDVLVNLAE RAYTLNYTCP TFIDKPGIRI TEGRHPVVEQ VLNEPFIANP
LNLSPQRRML IITGPNMGGK STYMRQTALI ALMAYIGSYV PAQKVEIGPI DRIFTRVGAA
DDLASGRSTF MVEMTETANI LHNATEYSLV LMDEIGRGTS TYDGLSLAWA CAENLANKIK
ALTLFATHYF ELTQLPEKME GVANVHLDAL EHGDTIAFMH SVQDGAASKS YGLAVAALAG
VPKEVIKRAR QKLRELESIS **PNAAATQVDG TQMSLLSVPE ETSPAVEALE NLDPDSLTPR
QALEWIYRLK SLV**
```

FIGURE 35. SEQ ID NO. 35: p53CDmut

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLD **PNAAATQVDG TQMSLLSVPE ETSPAVEALE
NLDPDSLTPR QALEWIYRLK SLV**
```

FIGURE 36. SEQ ID NO. 36: p63CDmut

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKR PNAAATQVDG TQMSLLSVPE
ETSPAVEALE NLDPDSLTPR QALEWIYRLK SLV
```

FIGURE 37. SEQ ID NO. 37: p73CDmut

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV PNAAATQVDG
TQMSLLSVPE ETSPAVEALE NLDPDSLTPR QALEWIYRLK SLV
```

FIGURE 38. SEQ ID No. 38: traM with tetramerization domain in bold

```
MAKVNLYISN DAYEKINAII EKRRQEGARE KDVSFSATAS MLLELGLRVH EAQMERKESA
FNQTEFNKLL LECVVKTQSS VAKILGIESL SPHVSGNSKF EYANMVEDIR EKVSSEMERF
FPKNDDE
```

FIGURE 39. SEQ ID NO. 39: p53CDtra

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLD QTEFNKLL LECVVKTQSS VAKILGIES
```

FIGURE 40. SEQ ID NO. 40: p63CDtra

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKR QTEFNKLL LECVVKTQSS VAKILGIES
```

FIGURE 41. SEQ ID NO. 41: p73CDtra

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV **QTEFNKLL LECVVKTQSS
VAKILGIES**
```

FIGURE 42. SEQ ID No: 42. GntR with tetramerization domain in bold

```
MKKKRPVLQD VADRVGVTKM TVSRFLRNPE QVSVALRGKI AAALDELGYI PNRAPDILSN
ATSRAIGVLL PSLTNQVFAE VLRGIESVTD AHGYQTMLAH YGYKPEMEQE RLESMLSWNI
DGLILTERTH TPRTLKMIEV AGIPVVELMD SKSPCLDIAV GFDNFEAARQ MTTAIIARGH
RHIAYLGARL DERTIIKQKG YEQAMLDAGL VPYSVMVEQS SSYSSGIELI RQARREYPQL
DGVFCTNDDL AVGAAFECQR LGLKVPDDMA IAGFHGHDIG QVMEPRLASV GAERLLARIR
GESVTPKMLD L LGFTLSPGGS I
```

FIGURE 43. SEQ ID NO. 43: p53CDgnt

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLD GESVTPKMLD LGFTLSPGGS I
```

FIGURE 44: SEQ ID NO: 44: p63CDgnt

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKR GESVTPKMLD LGFTLSPGGS I
```

FIGURE 45. SEQ ID NO. 45: p73CDgnt

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV **GESVTPKMLD
LGFTLSPGGS I**
```

FIGURE 46. SEQ ID No. 46: Lambda integrase with tetramerization domain in bold

```
**MGRRRSHERR DLPPNLYIRN NGYYCYRDPR TGKEFGLGRD RRIAITEAIQ ANIELFSGHK
HKPLTARINS DNS**VTLHSWL DRYEKILASR GIKQKTLINY MSKIKAIRRG LPDAPLEDIT
TKEIAAMLNG YIDEGKAASA KLIRSTLSDA FREAIAEGHI TTNHVAATRA AKSEVRRSRL
TADEYLKIYQ AAESSPCWLR LAMELAVVTG QRVGDLCEMK WSDIVDGYLY VEQSKTGVKI
AIPTALHIDA LGISMKETLD KCKEILGGET IIASTRREPL SSGTVSRYFM RARKASGLSF
EGDPPTFHEL RSLSARLYEK QISDKFAQHL LGHKSDTMAS QYRDDRGREW DKIEIK
```

FIGURE 47. SEQ ID NO. 47: p53CDint

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLD **MGRRRSHERR DLPPNLYIRN NGYYCYRDPR
TGKEFGLGRD RRIAITEAIQ ANIELFSGHK HKPLTARINS DNS**
```

FIGURE 48. SEQ ID NO. 48: p63CDint

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKR **MGRRRSHERR DLPPNLYIRN
NGYYCYRDPR TGKEFGLGRD RRIAITEAIQ ANIELFSGHK HKPLTARINS DNS**
```

FIGURE 49. SEQ ID NO. 49: p73CDint

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV **MGRRRSHERR
DLPPNLYIRN NGYYCYRDPR TGKEFGLGRD RRIAITEAIQ ANIELFSGHK HKPLTARINS
DNS**
```

FIGURE 50. SEQ ID No. 50: Measles virus phosphoprotein, tetramerization domain in bold MAEEQARHVK NGLECIRALK AEPIGSLAIE EAMAAWSEIS DNPGQERATC KEEKAGSSGL
SKPCLSAIGS TEGGAPRIRG QGSGESDDDA ETLGTPSGNL QASSAGLQRY YVYDHSGEAV
KGIQDADSIV VQSGLDGDST LSGGDNESEN SDVDIGEPDT EGYAITDRGF APISMGFRAS
DVETAEGGEI HELLRLQSRG NNFLKSGKTL NVPPPPDPGR ANTSETPIKK GTDARLASFG
TEIASLLTGG ATQCARKSPS EPSGLGAPAG NVPECVSNAA LIQEWTPESG TTISPRSQNN
EEGGDYY**DDE LFSDVQDIKT ALAKIHEDNQ KIISKLESLL LLKGEVESIK KQINKQNISI
STLEGHLSSI** MIAIPGFGKD PNDPTADVEI NPDLKPIISR DSGRALAEVL KKPVASRQLQ
GMTSGRTSSR GQLLKEFQLK PIGKKMSSAV GFVPDTGPAS RSVIRSIIKS SRLEEDRKRY
LMTLLDDIKG ANDLAKFHQM LMKIIMK

FIGURE 51. SEQ ID NO. 51: p53CDmea

MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLD **DDELFSDVQD IKTALAKIHE DNQKIISKLE
SLLLLKGEVE SIKKQINKQN ISISTLEGHL SSIM**

FIGURE 52. SEQ ID NO. 52: p63CDmea

MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKR **DDELFSDVQD IKTALAKIHE
DNQKIISKLE SLLLLKGEVE SIKKQINKQN ISISTLEGHL SSIM**

FIGURE 53. SEQ ID NO. 53: p73CDmea

MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV DDELFSDVQD
IKTALAKIHE DNQKIISKLE SLLLLKGEVE SIKKQINKQN ISISTLEGHL SSIM

FIGURE 54. SEQ ID No. 54: Nipah viral phosphoprotein, tetramerization domain in bold MDKLELVNDG LNIIDFIQKN QKEIQKTYGR SSIQQPSIKD QTKAWEDFLQ CTSGESEQVE
GGMSKDDGDV ERRNLEDLSS TSPTDGTIGK RVSNTRDWAE GSDDIQLDPV VTDVVYHDHG
GECTGYGFTS SPERGWSDYT SGANNGNVCL VSDAKMLSYA PEIAVSKEDR ETDLVHLENK
LSTTGLNPTA VPFTLRNLSD PAKDSPVIAE HYYGLGVKEQ NVGPQTSRNV NLDSIKLYTS
DDEEADQLEF EDEFAGSSSE VIVGISPEDE EPSSVGGKPN ESIGRTIEGQ SIRDNLQAKD
NKSTDVPGAG PKDSAVKEEP PQKRLPMLAE EFECSGSEDP IIRELLKENS LINCQQGKDA
QPPYHWSIER SISPDKTEIV NGAVQTADRQ RPGTPMPKSR GIPIKKGTDA KYPSAGTENV
PGSKSGATRH VRGSPPYQEG KSVNAENVQL NASTAVKETD KSEVNPVDDN DSLDDKYIMP
SDDFSNTFFP HDTDRLNYHA DHLGDYDLET LCEESVLMGV INSIKLINLD MRLNHIEEQV
KEIPKIINKL ESIDRVLAKT NTALSTIEGH LVSMMIMIPG KGKGERKGKN NPELKPVIGR
DILEQQSLFS FDNVKNFRDG SLTNEPYGAA VQLREDLILP ELNFEETNAS QFVPMADDSS
RDVIKTLIRT HIKDRELRSE LIGYLNKAEN DEEIQEIANT VNDIIDGNI

FIGURE 55. SEQ ID NO. 55: p53CDnip

MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLD YHADHLGDYD LETLCEESVL MGVINSIKLI
NLDMRLNHIE EQVKEIPKII NKLESIDRVL AKTNTALSTI EGHLVSMMI

FIGURE 56. SEQ ID NO. 56: p63CDnip

```
MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKR YHADHLGDYD LETLCEESVL
MGVINSIKLI NLDMRLNHIE EQVKEIPKII NKLESIDRVL AKTNTALSTI EGHLVSMMI
```

FIGURE 57. SEQ ID NO. 57: p73CDnip

```
MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV YHADHLGDYD
LETLCEESVL MGVINSIKLI NLDMRLNHIE EQVKEIPKII NKLESIDRVL AKTNTALSTI
EGHLVSMMI
```

FIGURE 58: SEQ ID No: 58: Tapeworm VASP, tetramerization domain in bold

```
PPPPPPPPPP PPPPPSQSAS ASSLQSMNNE HKASTASALS DLPHDLHAAY PNDTDVGSSG
GGGGWLATQL RLAKQQRMQR QQTATGVGDS TSASGGQTGI PGGTGTLSRA VGADMMSDLQ
RVLAARRRAR EGDTDETDGD ATATGVAACN DTNYSTTGHY RRPSQSSNPS NHNNNSTTAT
YATPVAPSQT PSAYGTIRKN STSVISSDSS GTQTITRADL ETFKREILAE FRKEVKSLKS
EILDALRVSN NRLS
```

FIGURE 59. SEQ ID NO. 59: p53CDvasp

```
MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
```

RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLD ADLETFKREI LAEFRKEVKS LKSEILDALR

FIGURE 60: SEQ ID NO: 60: p63CDvasp

MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKR **ADLETFKREI LAEFRKEVKS
LKSEILDALR**

FIGURE 61. SEQ ID NO. 61: p73CDvasp

MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV **ADLETFKREI
LAEFRKEVKS LKSEILDALR**

FIGURE 62. SEQ ID No. 62: Chicken KCNA5, with tetramerization domain in bold MEIALVTLEN GGGGAISSVE YATAGSTSGS TRARRQSELL HTAGSTFVPR LSDGKEGTPP
PSPPPQVDEE RERLPPTPRG GGGRRCSSSE GSINGRAASG PQPQPHAPRS GPAAEMDPPE
EGGHRQGMTM AAAGDEEGMK AASRSAMHHQ RVLINISGLH FETQLGTLNQ FPDTLLGDPD
KRMRYFDPLR NEYFFDRNRP **SFDGILYFYQ SGGKLRRPVN VSIDVFADEI RFYQLGKEAM
ERFQEDEGFI** REQEKPLPHS EFQRQVWLIF EYPESSSSAR AIAIVSVLVI LISIITFCLE
TLPEFRDERE IPMSLPPQSG GLNATAGDSP PMQSPSSISD PFFIIETTCV IWFTFELLVR
FFTCPSKPEF SRNIMNIIDI VAIIPYFITL GTELAHEQQQ PGGSSNNGSG SQQQAMSLAI
LRVIRLVRVF RIFKLSRHSK GLQILGQTLK ASMRELGLLI FFLFIGVILF SSAAYFAEAD
DPESHFSSIP DAFWWAVVTM TTVGYGDMRP ITVGGKIVGS LCAIAGVLTI ALPVPVISN FNYFYHRETD HEEQAMLKEE HSSAQSSITG VDGKRRSSKN SLNKSVVHLE NNEGFKSASP
LEKTNIKAKS NVDLRKSLYA LCLDSSRETD L

FIGURE 63. SEQ ID NO. 63: p53CDkcna5

MEEPQSDPSV EPPLSQETFS DLWKLLPENN VLSPLPSQAM DDLMLSPDDI EQWFTEDPGP
DEAPRMPEAA PPVAPAPAAP TPAAPAPAPS WPLSSSVPSQ KTYQGSYGFR LGFLHSGTAK
SVTCTYSPAL NKMFCQLAKT CPVQLWVDST PPPGTRVRAM AIYKQSQHMT VVRRCPHHE
RCSDSDGLAP PQHLIRVEGN LRVEYLDDRN TFRHSVVVPY EPPEVGSDCT TIHYNYMCNS
SCMGGMNRRP ILTIITLEDS SGNLLGRNSF EVRVCACPGR DRRTEEENLR KKGEPHHELP
PGSTKRALPN NTSSSPQPKK KPLD **DGILYFYQ SGGKLRRPVN VSIDVFADEI RFYQLGKEAM
ERFQEDEGF**

FIGURE 64. SEQ ID NO. 64: p63CDkcna5

MNFETSRCAT LQYCPDPYIQ RFVETPAHFS WKESYYRSTM SQSTQTNEFL SPEVFQHIWD
FLEQPICSVQ PIDLNFVDEP SEDGATNKIE ISMDCIRMQD SDLSDPMWPQ YTNLGLLNSM
DQQIQNGSSS TSPYNTDHAQ NSVTAPSPYA QPSSTFDALS PSPAIPSNTD YPGPHSFDVS
FQQSSTAKSA TWTYSTELKK LYCQIAKTCP IQIKVMTPPP QGAVIRAMPV YKKAEHVTEV
VKRCPNHELS REFNEGQIAP PSHLIRVEGN SHAQYVEDPI TGRQSVLVPY EPPQVGTEFT
TVLYNFMCNS SCVGGMNRRP ILIIVTLETR DGQVLGRRCF EARICACPGR DRKADEDSIR
KQQVSDSTKN GDGTKRPFRQ NTHGIQMTSI KKR **DGILYFYQ SGGKLRRPVN VSIDVFADEI
RFYQLGKEAM ERFQEDEGF**

FIGURE 65. SEQ ID NO. 65: p73CDkcna5

MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV **DGILYFYQ SGGKLRRPVN
VSIDVFADEI RFYQLGKEAM ERFQEDEGF**

FIGURE 66. SEQ ID No. 66: Cat Cholinesterase, tetramerization domain in bold

```
MQSKGTIISI  QFLLRFLLLW  VLIGKSHTEE  DIIITTKNGK  VRGMNLPVLD  GTVTAFLGIP
YAQPPLGRLR  FKKPQFLTKW  SDIWNATKYA  NSCYQNADQS  FPGFPGSEMW  NPNTDLSEDC
LYLNVWIPTP  KPKNATVMIW  IYGGGFQTGT  SSLPVYDGKF  LARVERVIVV  SMNYRVGALG
FLALPGNPEV  PGNMGLFDQQ  LALQWVQKNI  AAFGGNPKSV  TLFGESAGAG  SVSLHLLSPR
SQPLFTRAIL  QSGSSNAPWA  VMSLDEAKNR  TLTLAKFIGC  SKENDTEIIK  CLRNKDPQEI
LLNELLVVPS  DTLLSVNFGP  VVDGDFLTDM  PDTLLQLGQF  KKTQILVGVN  KDEGTAFLVY
GAPGFSKDND  SIITRKEFQE  GLKIYFPGVS  EFGREAILFY  YVDLLDDQRA  EKYREALDDV
LGDYNIICPA  LEFTTKFSEL  GNNAFFYYFE  HRSSQLPWPE  WMGVMHGYEI  EFVFGLPLER
RVNYTRAEEI  LSRSIMNYWA  NFAKYGNPNG  TQNNSTRWPA  FRSTDQKYLT  LNAESPKVYT
KLRAQQCRFW  TLFFPKVLEM  TGNIDEAERE  WRAGFYRWNN  YMMDWKNQFN  DYTSKKESCA  GL
```

FIGURE 67. SEQ ID NO. 67: p53CDchol

```
MEEPQSDPSV  EPPLSQETFS  DLWKLLPENN  VLSPLPSQAM  DDLMLSPDDI  EQWFTEDPGP
DEAPRMPEAA  PPVAPAPAAP  TPAAPAPAPS  WPLSSSVPSQ  KTYQGSYGFR  LGFLHSGTAK
SVTCTYSPAL  NKMFCQLAKT  CPVQLWVDST  PPPGTRVRAM  AIYKQSQHMT  VVRRCPHHE
RCSDSDGLAP  PQHLIRVEGN  LRVEYLDDRN  TFRHSVVVPY  EPPEVGSDCT  TIHYNYMCNS
SCMGGMNRRP  ILTIITLEDS  SGNLLGRNSF  EVRVCACPGR  DRRTEEENLR  KKGEPHHELP
PGSTKRALPN  NTSSSPQPKK  KPLD  DEAEREWRAG  FYRWNNYMMD  WKNQFNDYTS  KKESCAG
```

FIGURE 68. SEQ ID NO. 68: p63CDchol

```
MNFETSRCAT  LQYCPDPYIQ  RFVETPAHFS  WKESYYRSTM  SQSTQTNEFL  SPEVFQHIWD
FLEQPICSVQ  PIDLNFVDEP  SEDGATNKIE  ISMDCIRMQD  SDLSDPMWPQ  YTNLGLLNSM
DQQIQNGSSS  TSPYNTDHAQ  NSVTAPSPYA  QPSSTFDALS  PSPAIPSNTD  YPGPHSFDVS
FQQSSTAKSA  TWTYSTELKK  LYCQIAKTCP  IQIKVMTPPP  QGAVIRAMPV  YKKAEHVTEV
VKRCPNHELS  REFNEGQIAP  PSHLIRVEGN  SHAQYVEDPI  TGRQSVLPY  EPPQVGTEFT
TVLYNFMCNS  SCVGGMNRRP  ILIIVTLETR  DGQVLGRRCF  EARICACPGR  DRKADEDSIR
KQQVSDSTKN  GDGTKRPFRQ  NTHGIQMTSI  KKR  **DEAEREWRAG  FYRWNNYMMD
WKNQFNDYTS  KKESCAG**
```

FIGURE 69. SEQ ID NO. 69: p73CDchol

MAQSTATSPD GGTTFEHLWS SLEPDSTYFD LPQSSRGNNE VVGGTDSSMD VFHLEGMTTS
VMAQFNLLSS TMDQMSSRAA SASPYTPEHA ASVPTHSPYA QPSSTFDTMS PAPVIPSNTD
YPGPHHFEVT FQQSSTAKSA TWTYSPLLKK LYCQIAKTCP IQIKVSTPPP PGTAIRAMPV
YKKAEHVTDV VKRCPNHELG RDFNEGQSAP ASHLIRVEGN NLSQYVDDPV TGRQSVVVPY
EPPQVGTEFT TILYNFMCNS SCVGGMNRRP ILIIITLEMR DGQVLGRRSF EGRICACPGR
DRKADEDHYR EQQALNESSA KNGAASKRAF KQSPPAVPAL GAGV **DEAEREWRAG
FYRWNNYMMD WKNQFNDYTS KKESCAG**

P53, P63, AND P73 HOMO-TETRAMERIC COMPOSITIONS

CROSS-REFERENCE TO RELATED APPLICATIONS

This application claims priority to U.S. Ser. No. 63/243,059, filed Sep. 10, 2021, and incorporated by reference in its entirety for all purposes.

FEDERALLY SPONSORED RESEARCH AND DEVELOPMENT

Not applicable.

JOINT RESEARCH AGREEMENT

Not applicable.

REFERENCE TO ELECTRONIC SEQUENCE LISTING

The application contains a Sequence Listing which has been submitted electronically in .XML format and is hereby incorporated by reference in its entirety. Said .XML copy, created on Oct. 7, 2022, is named "TWISTER-PS3-005US02.xml" and is 116.122 bytes in size. The sequence listing contained in this .XML file is part of the specification and is hereby incorporated by reference herein in its entirety.

PRIOR ART

The disclosure generally relates to methods of treating cancer, autoimmune diseases, and autoinflammatory diseases using gene therapy and a combination of multiple methods to deliver gene therapy with modified p53, p63 and p73 tetramers.

BACKGROUND OF THE INVENTION

Cancer is a phenomenon of uncontrolled growth that can occur in any cell type. While the COVID-19 pandemic has made estimations challenging, according to the National Cancer Institute (NCI), over 1.8 million Americans were diagnosed with some form of cancer and over a third of them likely died from the disease in 2020. The NCI lists the current top five cancer types as breast cancer, lung/bronchus cancer, prostate cancer, colon/rectum cancer, and melanoma of the skin.

There are many methods used to treat cancer, depending on the type, location, and severity of disease. These include surgery to remove the tumor; chemical and radiological therapy to preferentially kill fast growing cells; immunotherapy; hormone therapy; stem cell therapy; and gene therapy. While not yet fully appreciated and formulated, gene therapy has the potential to provide personalized medicine. The delivery of the gene therapy payload needs to be safe, efficient, and targeted to only diseased cells (i.e., cancer or tumor cells), but the identity of the payload is also important.

In a normal cell, the genome is replicated during the S phase (or synthesis phase) of the eukaryotic cell cycle. This ensures that there are two copies of the genome that can be subsequently passed on to each daughter cell upon cell division. Under normal circumstances when DNA damage is detected, p53 (gene is TP53) as a tumor suppressor halts the cell cycle from proceeding to allow the cell time to repair the damage. If the damage is so extensive it cannot be repaired, then p53 as the "guardian of the genome" activates apoptosis, causing the cell to die. p53's role ensures that only cells that are regulated "correctly" in their growth can persist and those that have lost this regulation will die and not lead to cancer. This guardian role is underscored by the fact that in almost all cancers, p53 is not present, mutated or misregulated, which contributes to the cancer's uncontrolled cell division.

Early studies that tried to treat cancer cells with a mutated p53 protein discovered that expressing wildtype p53 protein in these cells did not have the desired therapeutic effect of treating the cancer. Since p53 functions as a homo-tetramer, even if one of those monomers within the tetramer were the mutation version, then the tetramer was poisoned and could not function properly. This is referred to as a dominant negative effect, where one mutated monomer can negate the functionality of three wildtype monomers in the same complex.

Other studies have shown that this dominant negative effect can be overcome if wildtype p53 is expressed at a high enough rate, such as through a viral vector, to where sufficient quantities of fully wildtype tetramers are made to treat cancer. However, there are challenges with using viral vectors in gene therapy, such as the potential for erroneous integration in the genome by viral vector, inability to control which cells are infected (diseased or healthy), reaction by the immune system, inability to give more than one treatment dosage, and potential for side effects associated with too high expression of the viral cassette; thus, it is expected to be difficult to express wildtype P53 in patients in a precise and controlled manner using a viral vector.

The p53 (Acc. No. P04637) tumor suppressor monomer is a 393-amino acid protein that has six domains: an N-terminal transactivation domain (residues 1-42); a proline-rich domain (residues 61-92); a central site-specific DNA-binding domain (residues 101-300); a nuclear localization signal (residues 305-322); a tetramerization domain (residues 325-356); and a C-terminal basic domain (residues 364-393) that is negatively regulated through interactions with cell cycle regulators.

p53 is also part of a family of tumor suppressors with similar structure and function. There is growing evidence that p63 (Q9H3D4) and p73 (O15350) (encoded by genes TP63 and TP73, respectively), while themselves not as frequently mutated in cancer as p53, have overlapping functions with p53 and may also contribute to tumor formation and progression. Both proteins can transactivate p53-responsive genes and can arrest the cell cycle for DNA repair. Both p63 and p73 have the same domain architecture and form homo-tetramers like p53, but they also have additional sequences on their C-termini, including a second proline-rich region and a sterile alpha motif (SAM). SAM is thought to be a protein-protein interaction domain with signaling proteins and transcription factors. p63 and p73 have evolved their own unique roles in the cell and are not functionally redundant for p53.

p53 has also been implicated in the differentiation of regulatory T cells, and this action suppresses autoimmunity. Thus, when misregulated or mutated, p53 appears to be involved in the development of autoimmune and autoinflammatory diseases, in addition to cancer.

Given that this family of proteins all behave as tetramers and that p53 demonstrates the aforementioned dominant negative phenotype, what is needed in the art is a way to express a p53 monomer (or the p63 or p73 monomers, respectively) that will only associate with itself (self-associate) to form functional homo-tetramers and never associate with a mutant p53 monomer (or mutant p63 or p73 monomer, respectively). The ideal method would be to change out the native tetramerization domain to a different sequence, such that binding to the mutant form is rendered impossible and only self-tetramers form.

SUMMARY OF THE INVENTION

This application focuses on a way to make an effective treatment for cancer, autoimmune diseases, and autoinflammatory diseases by overcoming the effects of a mutated version of p53 with a functional copy of p53 that only self-associates. Past therapies have failed because the p53 monomer could interact with the mutated p53, and a single mutant in the tetramer rendered it nonfunctional. Here we have devised a way to change p53 so it can only associate with like-monomers. This mechanism can also be applied to functional copies of p63 and p73 to interact only with other functional copies of p63 and p73, respectively.

To combat the dominant negative effect when a mutant p53 is present, p53 is truncated at about the beginning of the oligomerization domain (e.g., at 328) to form what we call "p53CD (1-327)" which is a C-terminal deletion ("CD") that lacks the native p53 tetramerization domain. It is expected that a small degree of leeway is allowed at the truncation site (+/−5-10 residues).

Nonetheless, to allow for tetramers to form, p53CD (1-327) is fused in frame with the tetramerization domain of the *Escherichia coli* lactose repressor (P03023, amino acids 336-360), the fusion protein referred to as p53CDlac.

Other tetramer associating sequences could be used, and in fact prior workers have tried the yeast dimerization domain from yeast GCN4 and human BCR, but domains from prokaryotic and viral sources are evolutionarily less similar and will have less potential to interact with any human sequence. This is important to avoid any inadvertent hetero-tetramers or dimers with other proteins in the human cell, thus interfering with their function, as well as the function of the new fusion proteins. Another option would be to use non-human proteins for the homo-tetramerization domain, being careful to ensure minimal homologies with any human proteins (<50%, or that number required to avoid any oligomerization therewith) and that the chosen domain is not capable of hetero-tetramers or dimers, and only makes homo-tetramers.

One advantage of using the LacI tetramerization domain is that it is of a prokaryotic origin and should have a significantly reduced tendency to interact with any human proteins; thus, p53CDlac should form tetramers only with itself and not interact with any other human protein through the LacI domain. However, where prokaryotic, viral other non-human sequences are used, it may be preferred to codon optimize for human use. This has the added benefits of efficient translation of therapeutic fusion proteins and minimalization of any transcriptional silencing effects from cellular recognition of tetramerization domains of non-human origin. In addition, where bacterial and viral sequences are used, it may be preferred to minimize the CpG content.

Another advantage of our approach is that p53CDlac (and any of the derivations described herein) will always remain intracellular (i.e., there will not be any immune system response to the tetramerization domains of prokaryotic or viral origin) to affect only the cell that is expressing this fusion protein.

The fusion variants of p53, p63 and p73 are predicted to be an effective therapy regardless of the cellular context of the native proteins, and the evidence available to date supports that (Okal, 2013).

While similar truncations can be made with p63 and p73, but in these instances, it may be preferred to excise only the native tetramerization domain, leaving some of the remaining carboxy terminal sequences. The tetramerization domains of these proteins are located at amino acids 394-443 and at 345-386, respectively per UniProt, and thus the truncated protein would be on or about p63(1-393) and p74(1-344), again with some amount of variation in truncation position still providing functionality and possibly with the remaining non-oligomerization C-terminal sequences retained.

If the p63 and p73 fusion proteins are to be used together or with a p53 fusion protein, then different tetramerization domains should be used, but where used separately, they can use the same lac repressor tetramerization domain or similar domain from a prokaryotic or bacteriophage/viral source or non-human source.

The order of choosing which tetramerization domain to use is that prokaryotic or bacteriophage/viral sequences are preferred. Next would be eukaryotic, but with no known homolog in human, such as fungal and other species less evolutionarily similar to human. Lastly, it would be eukaryotic origin, where a homolog may exist in humans, but where the domain is from a protein that is not nuclear in its subcellular localization.

Alternative tetramerization domains from prokaryotic and viral sources include any number of four helical bundle coiled-coil domains, such as MatP (P0A8N0), MutS (P23909), traM (P10026), GntR (P0ACP5), bacteriophage Lambda integrase (P03700), Measles virus phosphoprotein (B1GX97), and Nipah virus phosphoprotein (Q91K91). Eukaryotic sources include tapeworm VASP (A0A0X3P3Y2), chicken KCNA5 (A0A3Q2TS79), and cat cholinesterase (O62760).

The therapeutic p53, p63, and p73 fusion proteins can be delivered either as purified protein or encoded on a viral vector (such as adenoviral vector, adeno-associated viral vector, lentiviral vector, pox virus, alphavirus, herpes virus, and the like), a nonviral vector (such as MiniVector, minicircle, ministering, doggiebone DNA, mini-intronic plasmid, plasmid, or cosmid), or an RNA vector (such as mRNA). Preferred delivery mechanisms use the MiniVector, applied directly or via cells that contain same.

The expression of p53, p63, and p73 fusion proteins can be controlled by the CMV promoter, EF1α, CAG, PGK1, UBC, or any other promoter suitable for mammalian RNA polymerase II use. RNA polymerase II is preferred over RNA polymerase I and III. RNA polymerase I promoters are discouraged because this RNA polymerase is dedicated to the transcription of ribosomal genes and competition with this process could be harmful. RNA polymerase III does not synthesize long transcripts and would not be suitable for the longer transcripts needed for p53CDlac (and other fusion protein derivations described herein). Terminators can be the SV40 poly A terminator, human growth hormone terminator, bovine growth hormone terminator, rbGlob terminator, T1 terminator, or other appropriate terminator. Additional modules may be added to any expression vector as elements, including enhancer sequences such as CMV early enhancer, nuclear localization sites such as the SV40 early promoter, S/MAR sequence, CpG motifs, intron sequences, and the like.

The therapeutic p53, p63, and p73 fusion proteins can be used to treat any cancer or autoimmune or inflammatory disease where the native p53, p63, and p73 are not present, mutant, or misregulated. Therapy can be by gene delivery, mRNA delivery, or delivery of the purified protein alone or the protein decorated with cell-targeting groups, chemical moieties, aptamers, biologics, cell-penetrating peptides, monoclonal antibodies, stapled peptides, and the like.

The therapeutic payload can be delivered as is or complexed in solution. "Solutions" comprise a liquid mixture in which the minor component (the solute) is uniformly distributed within the major component (the solvent). Solutions can be ionic or non-ionic.

Methods to transfer the therapeutic payload into recipient cells or into a differentiated tissue by transfection include, for example, PEI, lipofection, electroporation, cationic liposomes, or any other method of transfection, or any method used to introduce DNA into cells or tissues, for instance, jet injection, jet or mesh nebulization, sonoporation, electroporation, mechanical acceleration (gene gun, etc.), or any other method of transfer.

The therapeutic payload may be delivered in a gel, hydrogel, a matrix, mesoporous silica, nanostructure silicone, a solution, a nanoparticle, natural vesicle (i.e., exosome and the like), a cell, or other means directly into tumor or residual tumor cells or tissue, or into cells ex vivo that are then returned to a patient. Typically, in vivo studies use injection or surgical introduction, but any method can be used ex vivo. It is well known by those skilled in the art that the term "cell" includes Car T cells or any cell therapy.

"Aqueous solutions" are those where the solvent is water-based. Aqueous solutions can optionally comprise a variety of additive components including salt or salts (e.g., saline), ether, buffers, acids such as lactic acid or salicylic acid or hydrochloric acid, bases, transfection agents such as lipofectamine, hydrocarbons such as glycerol or vegetable oils, polyamines such as putrescine, spermidine, and spermine, sugars, polymers such as polylysine and polyethylene glycol and their variants, surfactants, detergents such as tween-80, and inorganic materials (such as ceramics or ceramic powders). Additive components may be functionalized to enhance biocompatibility or solution properties.

"Non-aqueous solutions" are those where the solvent is not water-based. A therapeutic non-aqueous solution could comprise a lipid-based system for example. Phenol is an optional additive along with antioxidants such as alpha-tocopherol or thioglycolic acid or beta-carotene.

"Emulsion" is understood to comprise a dispersion of one material (i.e., a phase) in another in which it is not soluble or miscible. Emulsions could be employed for the purpose of facilitating or retarding spreading in vivo. Example emulsion components could include a perfluorocarbon. Emulsions can optionally affect the rate of MiniVector delivery or other therapeutic agents combined with Mini-Vectors. Non-solubilized phases could be micro or nano-sized. The location of the delivery could also be affected by varying pH, spreading, or adhesion propensity.

"Gels" can be applied topically during surgery, injected, or formed in situ through control of order of component addition. Gels formed in vivo would comprise reaction products that react locally at or near the injection site. The gel can be comprised of polymers such as polyethylene glycol and its variants, hydrogels, inorganic materials, membranes, carbohydrates, or other materials.

"Matrices" can be comprised of mesoporous silica, nanostructure silicone, fibers, cloths, membranes, polymers, metals, or hybrids thereof. The matrix can optionally be solubilized by the body or an active agent added ex vivo or in vivo during or after implantation in the patient. MiniVectors can be infused into matrices ex vivo (preferred) or in vivo.

"Nanoparticles" are understood to comprise particles in any dimension that are less than 1,000 nanometers, more preferably less than 500 nanometers, and most preferably less than 300 nanometers. The nanoparticle can be a viral vector, a component of a viral vector (e.g., a capsid), a non-viral vector (e.g., a plasmid or RNA), a cell, a fullerene and its variants, a small molecule, a peptide, protein, metal and oxides thereof, etc.

The term "treating" includes both therapeutic treatment and prophylactic treatment (reducing the likelihood of disease development). The term means decrease, suppress, attenuate, diminish, arrest, or stabilize the development or progression of a disease (e.g., a disease or disorder delineated herein), lessen the severity of the disease, or improve the symptoms associated with the disease.

As used herein, "MiniVector" means a double stranded, supercoiled, and circular DNA encoding an open reading frame of interest (e.g., a truncated p53 fusion) that can be expressed in a mammalian cell, said MiniVector lacking a bacterial origin of replication and lacking an antibiotic resistance gene, and being is at least 99% pure, preferably >99.5% or >99.8% of other DNA contaminants, is CpG minimized or CpG free as compared to parental sequences, and said composition can thereby be used to repeatedly treat an cancer patient since the immunogenicity and gene silencing effect of the MinVector is greatly reduced as compared with all other expression vectors.

As used herein, "isolated" means it has been removed from its native environment, e.g., an isolated DNA is no longer present in the native genome but has been removed therefrom. "Purified" by contrast means that >50% of any cell material has been removed, including protein, nucleic acids, lipids and the like leaving a purified protein or DNA.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim. The phrase "consisting of" is closed, and excludes all additional elements. The phrase "consisting essentially of" excludes additional material elements, but allows the inclusions of non-material elements that do not substantially change the nature of the invention, such as instructions for use, buffers, excipients, solvents, and the like. Any claim or claim element introduced with the open transition term "comprising," may also be narrowed to use the phrases "consisting essentially of" or "consisting of." However, the entirety of claim language is not repeated verbatim in the interest of brevity herein.

The following abbreviations are used herein:

| ABBREVIATION | TERM |
| --- | --- |
| Akt | Protein Kinase B (AKR mouse strain, thymoma) |
| BCR | Breakpoint cluster region |
| Cad11 | Cadherin 11 |
| CAG | Synthetic promoter of cytomegalovirus early enhancer element, the |

-continued

| ABBREVIATION | TERM |
|---|---|
| | promoter, first exon and first intron of chicken beta-actin gene, and the splice acceptor of the rabbit beta-globin gene |
| CD | C-terminal deletion or truncation |
| CMV | Cytomegalovirus, herein we use the CMV promoter |
| CpG | Cytosine followed by guanine in DNA; site of methylation |
| DNA | Deoxyribonucleic acid |
| EF1a | Elongation factor 1 alpha |
| ELISA | Enzyme-linked immunosorbent assay |
| FoxM1 | Forkhead Box M1 |
| GCN4 | General Control Nondepressible 4 transcriptional activator |
| GntR | Gluconate repressor |
| KCNA5 | Potassium Voltage-Gated Channel Subfamily A Member 5 |
| IL-12 | Interleukin 12 |
| LacI | Lactose Repressor |
| MatP | Macrodomain Ter protein |
| Mdm2 | Murine double minute 2 (E3 ubiquitin-protein ligase) |
| MutS | DNA mismatch repair protein |
| NCI | National Cancer Institute |
| PEG | Polyethyleglycol |
| PEI | Polyethylenimine |
| PGK1 | Phosphoglycerate Kinase 1 |
| rbGlob | recombinant bovine growth hormone terminator |
| RNA | Ribonucleic acid |
| RNAa | RNA activation |
| RNAi | RNA interference |
| S/MAR | Scaffold / Matrix attachment region |
| SAM | sterile alpha motif |
| SDS-PAGE | Sodium docecyl sulfate-polyacrylamide gel electrophoresis |
| shRNA | Short hairpin ribonucleic acid |
| STAT-1 | Signal transducer and activator of transcription 1 |
| STAT-6 | Signal transducer and activator of transcription 6 |
| SV40 | Simian Vacuolating Virus 40 |
| TGF-β | Transforming Growth Factor beta |
| TP53 | p53 gene |
| TP63 | p63 gene |
| TP73 | p73 gene |
| traM | Relaxosome protein |
| UBC | Polyubiquitin C |
| VASP | Vasodilator-stimulated phosphoprotein |

BRIEF DESCRIPTION OF DRAWINGS

FIG. 1. SEQ ID NO. 1: p53 with oligomerization domain in bold.
FIG. 2. SEQ ID NO. 2: p63 with oligomerization domain in bold.
FIG. 3. SEQ ID NO. 3: p73 with oligomerization domain in bold.
FIG. 4. SEQ ID NO. 4: Lac Repressor with tetramerization domain in bold.
FIG. 5 SEQ ID NO. 5: p53CDlac (v1).
FIG. 6. SEQ ID NO. 6: MiniVector encoding CMV-p53CDlac (v1) sequence.
FIG. 7. SEQ ID NO. 7: p53CDlac (v2).
FIG. 8. SEQ ID NO. 8: p53CDlac (v3).
FIG. 9. SEQ ID NO. 9: p53CDlac (v4).
FIG. 10. SEQ ID NO. 10: p53CDlac (v5).
FIG. 11. SEQ ID NO. 11: p53CDlac (v6).
FIG. 12. SEQ ID NO. 12: p53CDlac (v7).
FIG. 13. SEQ ID NO. 13: p53CDlac (v8).
FIG. 14. SEQ ID NO. 14: p63CDlac (v1).
FIG. 15. SEQ ID NO. 15: p63CDlac (v2).
FIG. 16. SEQ ID NO. 16: p63CDlac (v3).
FIG. 17. SEQ ID NO. 17: p63CDlac (v4).
FIG. 18. SEQ ID NO. 18: p63CDlac (v5).
FIG. 19. SEQ ID NO. 19: p63CDlac (v6).
FIG. 20. SEQ ID NO. 20: p63CDlac (v7).
FIG. 21. SEQ ID NO. 21: p63CDlac (v8).
FIG. 22. SEQ ID NO. 22: p73CDlac (v1).
FIG. 23. SEQ ID NO. 23: p73CDlac (v2).
FIG. 24. SEQ ID NO. 24: p73CDlac (v3).
FIG. 25. SEQ ID NO. 25: p73CDlac (v4).
FIG. 26. SEQ ID NO. 26: p73CDlac (v5).
FIG. 27. SEQ ID NO. 27: p73CDlac (v6).
FIG. 28. SEQ ID NO. 28: p73CDlac (v7).
FIG. 29. SEQ ID NO. 29: p73CDlac (v8).
FIG. 30. SEQ ID NO. 30: MatP with tetramerization domain in bold.
FIG. 31. SEQ ID NO. 31: p53CDmat.
FIG. 32. SEQ ID NO. 32: p63CDmat.
FIG. 33. SEQ ID NO. 33: p73CDmat.
FIG. 34. SEQ ID NO. 34: MutS with tetramerization domain in bold.
FIG. 35. SEQ ID NO. 35: p53CDmut.
FIG. 36. SEQ ID NO. 36: p63CDmut.
FIG. 37. SEQ ID NO. 37: p73CDmut.
FIG. 38. SEQ ID NO. 38: traM with tetramerization domain in bold.
FIG. 39. SEQ ID NO. 39: p53CDtra.
FIG. 40. SEQ ID NO. 40: p63CDtra.
FIG. 41. SEQ ID NO. 41: p73CDtra.
FIG. 42. SEQ ID NO. 42: GntR with tetramerization domain in bold.
FIG. 43. SEQ ID NO. 43: p53CDgnt.
FIG. 44. SEQ ID NO. 44: p63CDgnt.
FIG. 45. SEQ ID NO. 45: p73CDgnt.
FIG. 46. SEQ ID NO. 46: Lambda integrase with tetramerization domain in bold.
FIG. 47. SEQ ID NO. 47: p53CDint.
FIG. 48. SEQ ID NO. 48: p63CDint.
FIG. 49. SEQ ID NO. 49: p73CDint.
FIG. 50. SEQ ID NO. 50: Measles virus phosphoprotein with tetramerization domain in bold.
FIG. 51. SEQ ID NO. 51: p53CDmea.
FIG. 52. SEQ ID NO. 52: p63CDmea.
FIG. 53. SEQ ID NO. 53: p73CDmea.
FIG. 54. SEQ ID NO. 54: Nipah viral phosphoprotein with tetramerization domain in bold.
FIG. 55. SEQ ID NO. 55: p53CDnip.
FIG. 56. SEQ ID NO. 56: p63CDnip.
FIG. 57. SEQ ID NO. 57: p73CDnip.
FIG. 58. SEQ ID NO. 58: Tapeworm VASP with tetramerization domain in bold.
FIG. 59. SEQ ID NO. 59: p53CDvasp.
FIG. 60. SEQ ID NO. 60: p63CDvasp.
FIG. 61. SEQ ID NO. 61: p73CDvasp.
FIG. 62. SEQ ID NO. 62: Chicken Potassium Voltage-Gated Channel Subfamily A Member 5 (KCNA5) with tetramerization domain in bold.
FIG. 63. SEQ ID NO. 63: p53CDkcna5.
FIG. 64. SEQ ID NO. 64: p63CDkcna5.
FIG. 65. SEQ ID NO. 65: p73CDkcna5.
FIG. 66. SEQ ID NO. 66: Cat Cholinesterase with tetramerization domain in bold.
FIG. 67. SEQ ID NO. 67: p53CDchol.
FIG. 68. SEQ ID NO. 68: p63CDchol.
FIG. 69. SEQ ID NO. 69: p73CDchol.

DETAILED DESCRIPTION OF THE INVENTION

The disclosure provides novel assembly of modified p53, p63, and p73 tetramers in order to treat cancer, autoimmune diseases, and autoinflammatory diseases.

The invention includes any one or more of the following embodiment(s) in any combination(s) thereof, but each possible combination is not separately listed in the interests of brevity. In addition, comprising, consisting of or and consisting essentially of may all be used to introduce claim elements, but are not separately listed in the interests of brevity.

An isolated DNA encoding an expressable fusion protein, said fusion protein being a mutant p53 or p63 or p73 protein lacking a native tetramerization domain and being fused in frame to a prokaryotic or a viral or a non-human homo-tetramerization domain, said DNA capable of expressing said fusion protein in a human or bacterial cell and said fusion protein capable of homo-tetramerization only, but not homo-dimerization or hetero-dimerization or hetero-tetramerization.

Any DNA herein described, said DNA operably linked to a promoter and a terminator or optionally an enhancer.

Any DNA herein described, said DNA being a MiniVector, said MiniVector being a double stranded, supercoiled, circular DNA and lacking a bacterial origin of replication and lacking an antibiotic resistance gene, wherein said MiniVector is at least 99.98% pure of other DNA contaminants and is CpG minimized or CpG free as compared to parental sequences. The DNA may also be in the form of a plasmid, a viral vector, a cosmid, and the like.

An isolated fusion protein made from any DNA herein described, said fusion protein having DNA binding and transcriptional functions characteristic of wildtype p53 or wildtype p63 or wildtype p73. The mRNA encoding same is also a part of the invention.

An isolated fusion protein, said fusion protein comprising:
a) a p53 fusion protein consisting of amino acid residues 1 or 2 to between about 320 to about 340 of human p53 fused to a heterologous tetramerization domain from a prokaryotic protein or a viral protein, said p53 fusion protein being unable to form hetero-tetramers or dimers but able to form homo-tetramers and having tumor suppression activity; or
b) a p63 fusion protein consisting of amino acid residues 1 or 2 to between about 390 to about 405 of human p63 fused to a heterologous tetramerization domain from a prokaryotic protein or a viral protein, said p63 fusion protein being unable to form hetero-tetramers or dimers but able to form homo-tetramers and having tumor suppression activity; or
c) a p73 fusion protein consisting of amino acid residues 1 or 2 to between about 340 to about 355 of human p73 fused to a heterologous tetramerization domain from a prokaryotic protein or a viral protein, said p73 fusion protein being unable to form hetero-tetramers or dimers but able to form homo-tetramers and having tumor suppression activity.

A MiniVector expressably encoding any fusion protein herein described, said MiniVector being a double stranded, supercoiled, circular DNA and lacking a bacterial origin of replication and lacking an antibiotic resistance gene, wherein said MiniVector is at least 99.98% pure of other DNA contaminants and is CpG minimized or CpG free as compared to parental sequences.

A pharmaceutical comprising any DNA, RNA or protein herein described together with a pharmaceutically acceptable excipient.

An isolated DNA encoding a fusion protein expressable in a human and capable of homo-tetramerization but not hetero-tetramerization or dimerization, said DNA selected from a sequence encoding:
i) a p53 fusion protein selected from SEQ ID NO. 5-13, 31, 35, 39, 43, 47, 51, 55, 59, 63, or 67; or
ii) a p63 fusion protein selected from SEQ ID NO. 14-21, 32, 36, 40, 44, 48, 52, 56, 60, 64 or 68; or
iii) a p73 fusion protein selected from SEQ ID NO. 22-29, 33, 37, 41, 45, 49, 53, 57, 61, 65, or 69.

Preferably, such sequences are codon optimized for use in humans, and are CpG minimized where possible.

A method of treating cancer, comprising administering the fusion protein, or the DNA or the MiniVector or mRNA herein described to a patient with cancer in an amount effective to express said fusion protein and thereby treat said cancer. Similar methods can be used to treat autoimmune diseases or inflammatory diseases that have a p53, p63, or p73 component.

The present invention is exemplified with respect to the truncated p53 fusion, and cancer cell lines. However, this is exemplary only, and the invention can be broadly applied to variations in fusion points, truncated or excised p63 fusions, truncated or excised p73 fusions, and the treatments of other disease such as autoimmune and inflammatory diseases that are normally ameliorated by p53, p63, or p73.

The following examples are intended to be illustrative only, and not unduly limit the scope of the appended claims.

Making Fusion Proteins

The sequence encoding the first 327 amino acids of p53 (i.e., p53CD(1-327)) along with the sequence of the LacI tetramerization domain (amino acids 336-360) in frame will be cloned into the pNIC28 vector, which encodes any recombinant protein with an N-terminal histidine tag that can be removed using the Tobacco Etch Virus protease following protein purification. This plasmid is named pNIC28-p53CDlac and will be transformed into BL21(DE3) *Escherichia coli* with or without the pLysS episome.

To express p53CDlac, BL21(DE3) cells with or without pLysS are grown at 37° C. in Luria-Bertani Broth to mid-logarithmic growth as monitored by optical density at 600 nm, at which time, isopropyl-β-D-thiogalactopyranoside is added to induce expression of the recombinant protein. p53CDlac is overexpressed overnight at 37° C. The following day, the cells are harvested with centrifugation.

To purify p53CDlac, the harvested BL21(DE3) cells are lysed, either mechanically (i.e., French press or sonication) or enzymatically (i.e., lysozyme) and the lysis solution is centrifuged to separate the soluble protein fraction supernatant (where p53CDlac is located) from cellular debris. The supernatant is subjected to an ammonium sulfate precipitation where the precipitated protein fraction between 20-35% ammonium sulfate is resuspended in a buffer and applied to an immobilized metal affinity chromatography (IMAC) resin containing nickel; p53CDlac contains a his-tag and should bind the nickel resin. The resin is washed with buffer to remove all proteins that are not bound. p53CDlac is eluted from the resin and collected by adding a buffer containing imidazole. The eluant containing p53CDlac is dialyzed with buffer to remove the imidazole and is applied to a phosphocellulose (P-cell) cation exchange resin. The loaded P-cell resin is washed with buffer to remove all unbound proteins and p53CDlac is eluted from the P-cell resin by increasing the ionic strength of the buffer. Purified p53CDlac can then be used directly, or if needed, dialyzed into an appropriate buffer or pharmaceutical excipient prior to use.

Making Plasmids and Minivectors Encoding Fusion Proteins

The sequence encoding the first 327 amino acids of p53 (i.e., p53CD(1-327)) along with the sequence of the LacI tetramerization domain (amino acids 336-360) in frame will be cloned into the pMV parent vector used to generate MiniVectors. The p53CDlac sequence will be placed following a CMV promoter and upstream of a transcriptional terminator, such SV40 poly A terminator. This cassette of promoter, therapeutic payload, and terminator, as well as any other additions (including but not limited to enhancer sequences, nuclear localization sites, S/MAR sequence, CpG motifs, intron sequences, and the like) are placed between the attP and attB sites of the parent vector. The resulting vector, pMV-CMV-p53CDlac, will be generated in DH5α E. coli cells and purified using standard protocols in plasmid purification.

To generate MiniVectors, pMV-CMV-p53CDlac will be transformed into special E. coli bacterial host strain, LZ54 or LZ31, harboring λ-integrase (Int) under the control of the temperature sensitive cl857 repressor. When the cells have reached a suitable density, expression of Int is switched on by a temperature switch. Recombination results in a catenated product containing the MiniVector.

The products are decatenated, either by endonuclease cleavage of the large circle deletion product ex vivo, or by topoisomerase IV-mediated unlinking subsequent to the removal of topoisomerase inhibitor following the cell harvest.

The deletion product containing the undesired bacterial sequences is removed by PEG precipitation. Additional contaminants are removed by anion exchange chromatography and the final MiniVector is further purified by size exclusion chromatography, as described elsewhere yielding ultrapure, supercoiled MiniVector product that is 99.8 or 99.9 or 98.98% pure of plasmid parent and recombination side products.

If desired, the MiniVector can encode attR and the deletion product can contain attL by switching the positions of attB and attP in the parent plasmid.

Making mRNA Encoding Fusion Proteins

The sequence encoding the first 327 amino acids of p53 (i.e., p53CD(1-327)) along with the sequence of the LacI tetramerization domain (amino acids 336-360) in frame will be cloned following a CMV promoter and upstream of a transcriptional terminator, such SV40 poly A terminator. This cassette (CMV promoter, p53CDlac, and SV40 poly A terminator) will be encoded in a pUC18 vector where the Lac promoter (pLac) has been replaced with the T7 RNA polymerase promoter. In addition, the T7 terminator sequence will be placed C-terminal to the cassette. This vector, called pUC18-T7-CMV-p53CDlac, can be used for in vitro transcription of the mRNA encoding p53CDlac using recombinant T7 RNA polymerase. Following the transcription reaction, total RNA can be isolated using phenol-chloroform extractions followed by a series of alcohol washes with isopropanol and ethanol to pellet the RNA. The mRNA encoding p53CDlac can then be purified using commercial kits.

Making Viral Vectors Encoding Fusion Proteins

The sequence encoding the first 327 amino acids of p53 (i.e., p53CD(1-327)) along with the sequence of the LacI tetramerization domain (amino acids 336-360) in frame will be cloned following a CMV promoter and upstream of a transcriptional terminator, such SV40 poly A terminator. This cassette (CMV promoter, p53CDlac, and SV40 poly A terminator) will be cloned into a plasmid used to propagate and generate viral vectors (such as adenoviral vector, adeno-associated viral vector, lentiviral vector, pox virus, alphavirus, herpes virus, and the like) using a eukaryotic cell culture system. A commercial service to make and purify these viral particles may be used.

Cancer Treatment

The following prophetic examples can be applied equally to all cancers described herein, where p53 is not present, mutated, or misregulated. Wildtype p53 is most active during the S phase of the cell cycle and is activated through post-translational modifications in the C-terminal basic domain. A truncated version of p53 where the C-terminal domain is deleted (herein as p53CD(1-366)) has been shown to be constitutively active throughout the cell cycle. A further truncation that has the tetramerization domain deleted (herein p53CD(1-327)) should also be active so long as it can form a homo-tetramer using the lactose repressor or other tetramerization domain (LacI(336-360)). This therapeutic p53 fusion is designated p53CDlac.

To test the efficacy of p53CDlac, a human osteogenic sarcoma cell line (SAOS-LM6) will be transfected in cell culture with a MiniVector encoding p53CDlac under the control of the CMV promoter. The MiniVector will be complexed with polyethyleneimine (PEI) at an N:P ratio of 10:1. For seven days following transfection, the cell number and live/dead assays will be performed to show that p53CDlac is inhibiting the proliferation of SAOS-LM6 cells.

Following cell culture experiments, p53CDlac will be tested in a mouse lung metastasis model where SAOS-LM6 cells are injected IV into 4-to 6-week old specific-pathogen-free athymic male nude mice. After 5-6 weeks, metastases should be present in the lung and the mice will be treated by aerosol using a jet nebulizer or mesh nebulizer twice a week for four weeks using the same PEI-MiniVector in the cell culture experiment. Mice will be sacrificed after 12-13 weeks and their lunges will be resected, weighed, fixed, and examined under a dissection microscope for the presence of tumors. Alternatively, IV injection or injection directly into the tumor could be used for delivery.

In some mice, expression of p53CDlac will also be examined through immunohistochemistry of the lung tissue at 24-96 hours post-aerosol.

An alternative is the use of B16-F10 melanoma cell line in C57 BL/6 mice. This is a more aggressive lung metastasis model and the aerosol treatment will begin one day following the IV injection of the cancer cells into the mice.

Alternative methods to deliver the PEI-MiniVector may be more suitable and they include but are not limited to intravenous, intramuscular, intraperitoneal, topical, intravaginal, and rectal injections or applications. Delivery may also be facilitated by electroporation, sonoporation, electrosonoporation, or mechanical acceleration (gene gun, etc.).

In other examples, a plasmid (pMV-CMV-p53CDlac), an mRNA, a viral vector or purified p53CDlac protein can be delivered and assessed in both cell culture and mouse experiments described above. The same experiments can be conducted with p63 and p73 fusion proteins.

Another embodiment may involve other members of the p53 family, namely p63 and p73. A C-terminal deletion of p63 or p73 is used where their respective native tetramerization domains have been removed (p63CD or p73CD) and replaced with tetramerization domain of LacI (p63CDlac or p73CDlac). Here, p63CDlac or p73CDlac can be delivered on a MiniVector, plasmid, mRNA, viral vector, or as a purified protein. The therapy can be delivered and assessed in both the cell culture and mouse experiments described above. These fusion proteins can be used solo or together in various combinations.

In other examples, any of these fusion proteins can be used in combination with other cancer therapies including but limited to chemotherapy, radiotherapy, immunotherapy, surgery, CAR T, other biologics, specifically secreted biologics in vivo, any commercial and emerging technologies, and gene therapies by us and others. Gene therapy can include RNA interference (RNAi) and RNA activation (RNAa) technologies, in particular cancer specific shRNAs to FoxM1, Akt, Mdm2, and the like.

Autoimmune/Autoinflammatory Disease Therapy

The following prophetic examples can be applied to autoimmune and autoinflammatory diseases, where p53, p63, and/or p73 is not present, mutated, or misregulated. Autoimmune diabetes can be induced through low doses of streptozotocin in p53-deficient mice; thus, like in the cancer studies previously described, expressing a functional tetrameric p53, p63, or p73 can complement the deficiency in p53.

C57BL/6J mice heterozygous for p53 (i.e., p53$^{-/+}$) can be bred to produce homozygous wildtype (p53$^{+/+}$) and homozygous deficient or null (p53$^{-/-}$) mice. Autoimmune diabetes is induced in 7- to 9-week old male mice through intraperitoneal injection once a day for 5 consecutive days with 40 mg/kg body weight of streptozotocin. Mice are considered diabetic if urinary glucose levels are >500 mg/dl on two consecutive tests. Insulitis can be measured by fixing pancreata in 10% formalin, sectioning, staining with hematoxylin/eosin, and examining through microscopy.

To test the efficacy of p53CDlac in autoimmune diabetes, a MiniVector encoding p53CDlac under the control of the CMV promoter will be complexed with polyethyleneimine (PEI) at an N:P ratio of 10:1. Following streptozotocin treatment, p53$^{+/+}$ and p53$^{-/-}$ mice will be treated by aerosol using a jet nebulizer or mesh nebulizer twice a week for four weeks using the PEI-MiniVector. Urinary glucose levels and degree of insulitis can be measured during and following MiniVector treatment. To test cytokine production, spleen and pancreas are removed, homogenized, centrifuged, and the supernatants collected. Cytokine production can be measured using commercially-available ELISA kits.

An alternative measure of the treatment of autoimmune diabetes is to look at bone marrow-derived macrophages. The femurs and tibiae of the same mice used above can be removed and the marrow flushed with cell culture medium. Macrophages can be cultured. The cytokine production of these cells can be analyzed with flow cytometry and staining. In addition, macrophage cell lysates can be subjected to SDS-PAGE and western blotting for the levels and phosphorylation status of STAT-1, a transcriptional activator factor that is produced more and more highly phosphorylated in p53$^{-/-}$ mice.

As above, other modalities can be used, including plasmid vectors, cosmid vectors, viral vectors, mRNA, or protein, and the payloads can be delivered solo or in various combinations, and of course, promoters, terminators, enhancers and such can all be varied.

As above, other delivery methods can be used, including intravenous, intramuscular, intraperitoneal, topical, intravaginal, and rectal injections or applications. Delivery may also be facilitated by electroporation, sonoporation, electrosonoporation, or mechanical acceleration (gene gun, etc.).

As above, any of these fusion proteins can be used in combination with other therapies for autoimmune and autoinflammatory diseases, including immunotherapy, small molecule drug therapy, stem cell-derived therapy, and gene therapy such as RNAi and RNAa technologies, in particular autoimmune specific shRNAs to TGF-β, Cad11, STAT-6, IL-12, and the like.

The following references are incorporated by reference in their entirety for all purposes.

Waterman, M. J., et al., An engineered four-stranded coiled coil substitutes for the tetramerization domain of wildtype p53 and alleviates transdominant inhibition by tumor-derived p53 mutants, Cancer Research 56: 158-163 (1996).

Almazov V. P., et al., Construction of chimeric tumor suppressor p53 resistant to the dominant-negative interaction with p53 mutants, Mol Biol (Mosk) 36(4):664-71 (2002).

Gencel-Augusto J. & Lozano G., p53 tetramerization: at the center of the dominant-negative effect of mutant p53, Genes Dev. 34(17-18): 1128-1146 (2020).

Okal, A., et al., A chimeric p53 evades mutant p53 transdominant inhibition in cancer cells, Mol Pharm 10(10):3922-33 (2013).

U.S. Pat. No. 5,573,925 P53 proteins with altered tetramerization domains

US20020068283 Suppressor mutations for common P53 cancer mutations

US20160347806 Oligomerization domain of p53 to bypass the dominant-negative effect of mutant.

The invention claimed is:

1. An isolated DNA encoding a fusion protein expressable in a human and capable of homo-tetramerization but not hetero-tetramerization or dimerization, said DNA selected from a sequence encoding:
   i) a p53 fusion protein selected from SEQ ID No. 5, 7-13, 31, 35, 39, 43, 47, 51, 55, 59, 63, or 67; or
   ii) a p63 fusion protein selected from SEQ ID No. 14-21, 32, 36, 40, 44, 48, 52, 56, 60, 64 or 68; or
   iii) a p73 fusion protein selected from SEQ ID No. 22-29, 33, 37, 41, 45, 49, 53, 57, 61, 65, or 69.

2. A composition comprising a pharmaceutically acceptable excipient plus the DNA of claim 1.

3. An isolated DNA encoding an expressable fusion protein selected from SEQ ID No. 5, 7-29.

4. A composition comprising a pharmaceutically acceptable excipient plus the fusion protein encoded by the DNA of claim 1.

5. A composition comprising a pharmaceutically acceptable excipient plus i) the DNA of claim 3, or ii) a fusion protein encoded by the DNA of claim 3.

* * * * *

```
                           SEQUENCE LISTING

Sequence total quantity: 69
SEQ ID NO: 1            moltype = AA  length = 393
FEATURE                 Location/Qualifiers
REGION                  1..393
                        note = misc_feature - p53
source                  1..393
                        mol_type = protein
                        organism = Homo sapiens
SEQUENCE: 1
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRRCPHHE  180
RCSDSDGLAP PQHLIRVEGN LRVEYLDDRN TFRHSVVVPY EPPEVGSDCT TIHYNYMCNS  240
SCMGGMNRRP ILTIITLEDS SGNLLGRNSF EVRVCACPGR DRRTEEENLR KKGEPHHELP  300
PGSTKRALPN NTSSSPQPKK KPLDGEYFTL QIRGRERFEM FRELNEALEL KDAQAGKEPG  360
GSRAHSSHLK SKKGQSTSRH KKLMFKTEGP DSD                              393

SEQ ID NO: 2            moltype = AA  length = 680
```

```
FEATURE                 Location/Qualifiers
REGION                  1..680
                        note = misc_feature - p63
source                  1..680
                        mol_type = protein
                        organism = Homo sapiens
SEQUENCE: 2
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRRSPDDEL LYLPVRGRET YEMLLKIKES   420
LELMQYLPQH TIETYRQQQQ QQHQHLLQKQ TSIQSPSSYG NSSPPLNKMN SMNKLPSVSQ   480
LINPQQRNAL TPTTIPDGMG ANIPMMGTHM PMAGDMNGLS PTQALPPPLS MPSTSHCTPP   540
PPYPTDCSIV SFLARLGCSS CLDYFTTQGL TTIYQIEHYS MDDLASLKIP EQFRHAIWKG   600
ILDHRQLHEF SSPSHLLRTP SSASTVSVGS SETRGERVID AVRFTLRQTI SFPPRDEWND   660
FNFDMDARRN KQQRIKEEGE                                              680

SEQ ID NO: 3            moltype = AA  length = 635
FEATURE                 Location/Qualifiers
REGION                  1..635
                        note = misc_feature - p73
source                  1..635
                        mol_type = protein
                        organism = Homo sapiens
SEQUENCE: 3
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVKKRRHG DEDTYYLQVR   360
GRENFEILMK LKESLELMEL VPQPLVDSYR QQQQLLQRPS HLQPPSYGPV LSPMNKVHGG   420
MNKLPSVNQL VGQPPPHSSA ATPNLGPVGP MLNNHGHAVP ANGEMSSSHS AQSMVSGSHC   480
TPPPPYHADP SLVSFLTGLG CPNCIEYFTS QGLQSIYHLQ NLTIEDLGAL KIPEQYRMTI   540
WRGLQDLKQG HDYSTAQQLL RSSNAATISI GGSGELQRQR VMEAVHFRVR HTITIPNRGG   600
PGGGPDEWAD FGFDLPDCKA RKQPIKEEFT EAEIH                             635

SEQ ID NO: 4            moltype = AA  length = 360
FEATURE                 Location/Qualifiers
REGION                  1..360
                        note = misc_feature - Escherichia coli
source                  1..360
                        mol_type = protein
                        organism = Escherichia coli
SEQUENCE: 4
MKPVTLYDVA EYAGVSYQTV SRVVNQASHV SAKTREKVEA AMAELNYIPN RVAQQLAGKQ    60
SLLIGVATSS LALHAPSQIV AAIKSRADQL GASVVVSMVE RSGVEACKAA VHNLLAQRVS   120
GLIINYPLDD QDAIAVEAAC TNVPALFLDV SDQTPINSII FSHEDGTRLG VEHLVALGHQ   180
QIALLAGPLS SVSARLRLAG WHKYLTRNQI QPIAEREGDW SAMSGFQQTM QMLNEGIVPT   240
AMLVANDQMA LGAMRAITES GLRVGADISV VGYDDTEDSS CYIPPLTTIK QDFRLLGQTS   300
VDRLLQLSQG QAVKGNQLLP VSLVKRKTTL APNTQTASPR ALADSLMQLA RQVSRLESGQ   360

SEQ ID NO: 5            moltype = AA  length = 348
FEATURE                 Location/Qualifiers
REGION                  1..348
                        note = Synthetic: p53CDlac (v1)
source                  1..348
                        mol_type = protein
                        organism = synthetic construct
SEQUENCE: 5
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT VVRRCPHHER   180
CSDSDGLAPP QHLIRVEGNL RVEYLDDRNT FRHSVVVPYE PPEVGSDCTT IHYNYMCNSS   240
CMGGMNRRPI LTIITLEDSS GNLLGRNSFE VRVCACPGRD RTEEENLRK GEPHHELPP    300
GSTKRALPNN TSSSPQPKKK PLDTASPRAL ADSLMQLARQ VSRLESGQ                348

SEQ ID NO: 6            moltype = DNA  length = 2067
FEATURE                 Location/Qualifiers
misc_feature            1..2067
                        note = Synthetic: MiniVector encoding CMV-p53CDlac (v1)
source                  1..2067
                        mol_type = other DNA
                        organism = synthetic construct
SEQUENCE: 6
tttatactaa cttgagcgaa acgggaaggg tttgacattg attattgact agttattaat    60
```

```
agtaatcaat tacggggtca ttagttcata gcccatatat ggagttccgc gttacataac    120
ttacggtaaa tggcccgcct ggctgaccgc ccaacgaccc ccgcccattg acgtcaataa    180
tgacgtatgt tcccatagta acgccaatag ggactttcca ttgacgtcaa tgggtggagt    240
atttacggta aactgcccac ttggcagtac atcaagtgta tcatatgcca agtacgcccc    300
ctattgacgt caatgacggt aaatggcccg cctggcatta tgcccagtac atgaccttat    360
gggactttcc tacttggcag tacatctacg tattagtcat cgctattacc atggtgatgc    420
ggttttggca gtacatcaat gggcgtggat agcggtttga ctcacgggga tttccaagtc    480
tccaccccat tgacgtcaat gggagtttgt tttggcacca aaatcaacgg gactttccaa    540
aatgtcgtaa caactccgcc ccattgacgc aaatgggcgg taggcgtgta cggtgggagg    600
tctatataag cagagctctc tctggctaac tagagaaccc actgcttact ggcttatcga    660
aattaatacg actcactata gggagaccca agcttggtac catggaggag ccgcagtcag    720
atcctagcgt cgagccccct ctgagtcagg aaacattttc agacctatgg aaactacttc    780
ctgaaaacaa cgttctgtcc cccttgccgt cccaagcaat ggatgatttg atgctgtccc    840
cggacgatat tgaacaatgg ttcactgaag acccaggtcc agatgaagct cccagaatgc    900
cagaggctgc tccccccgtg gcccctgcac cagcagctcc tacaccggcg gcccctgcac    960
cagcccctc ctggccctg tcatcttctg tcccttccca gaaaacctac cagggcagct   1020
acggtttccg tctgggcttc ttgcattctg ggacagccaa gtctgtgact tgcacgtact   1080
cccctgccct caacaagatg ttttgccaac tggccaagac ctgccctgtg cagctgtggg   1140
ttgattccac accccccgcc ggcacccgcg tccgcgccat ggccatctac aagcagtcac   1200
agcacatgac ggaggttgtg aggcgctgcc ccaccatga gcgctgctca gatagcgatg   1260
gtctggcccc tcctcagcat cttatccgag tggaaggaaa tttgcgtgtg gagtatttgg   1320
atgacagaaa cacttttcga catagtgtgg tggtgcccta tgagccgcct ggagttggct   1380
ctgactgtac caccatccac tacaactaca tgtgtaacag ttcctgcatg ggcggcatga   1440
accggaggcc catcctcacc atcatcacac tggaagactc cagtggtaat ctactgggac   1500
ggaacagctt tgaggtgcgt gtttgtgcct gtcctgggag agaccggcgc acagaggaag   1560
agaatctccg caagaaaggg gagcctcacc acgagctgcc cccaggggac actaagcgag   1620
cactgcccaa caacaccagc tcctctcccc agcaaagaa gaaaccactg gatgagaat   1680
ataccgcctc tccccgcgcg ttggccgatt cattaatgca gctggcacga caggtttccc   1740
gactggaaag cgggcagtaa ttcgagcaga catgataaga tacattgatg agtttggaca   1800
aaccacaact agaatgcagt gaaaaaaatg ctttatttgt gaaatttgtg atgctattgc   1860
tttatttgta accattataa gctgcaataa acaagtttat ccgcgcaagc ttcctcagct   1920
ctgttacagg tcactaatac catctaagta gttgattcat agtgactgca tatgttgtgt   1980
tttacagtat tatgtagtct gttttttatg caaaatctaa tttaatatat tgatatttat   2040
atcatttta gtttctcgtt cagcttt                                       2067

SEQ ID NO: 7             moltype = AA   length = 346
FEATURE                  Location/Qualifiers
REGION                   1..346
                         note = Synthetic: p53CD1ac (v2)
source                   1..346
                         mol_type = protein
                         organism = synthetic construct
SEQUENCE: 7
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT VVRRCPHHER   180
CSDSDGLAPP QHLIRVEGNL RVEYLDDRNT FRHSVVVPYE PPEVGSDCTT IHYNYMCNSS   240
CMGGMNRRPI LTIITLEDSS GNLLGRNSFE VRVCACPGRD RRTEEENLRK KGEPHHELPP   300
GSTKRALPNN TSSSPQPKKK PLDSPRALAD SLMQLARQVS RLESGQ                  346

SEQ ID NO: 8             moltype = AA   length = 344
FEATURE                  Location/Qualifiers
REGION                   1..344
                         note = Synthetic: p53CD1ac (v3)
source                   1..344
                         mol_type = protein
                         organism = synthetic construct
SEQUENCE: 8
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT VVRRCPHHER   180
CSDSDGLAPP QHLIRVEGNL RVEYLDDRNT FRHSVVPYE PPEVGSDCTT IHYNYMCNSS    240
CMGGMNRRPI LTIITLEDSS GNLLGRNSFE VRVCACPGRD RRTEEENLRK KGEPHHELPP   300
GSTKRALPNN TSSSPQPKKK PLDRALADSL MQLARQVSRL ESGQ                    344

SEQ ID NO: 9             moltype = AA   length = 342
FEATURE                  Location/Qualifiers
REGION                   1..342
                         note = Synthetic: p53CD1ac (v4)
source                   1..342
                         mol_type = protein
                         organism = synthetic construct
SEQUENCE: 9
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT VVRRCPHHER   180
CSDSDGLAPP QHLIRVEGNL RVEYLDDRNT FRHSVVPYE PPEVGSDCTT IHYNYMCNSS    240
CMGGMNRRPI LTIITLEDSS GNLLGRNSFE VRVCACPGRD RRTEEENLRK KGEPHHELPP   300
GSTKRALPNN TSSSPQPKKK PLDLADSLMQ LARQVSRLES GQ                      342
```

```
SEQ ID NO: 10              moltype = AA  length = 340
FEATURE                    Location/Qualifiers
REGION                     1..340
                           note = Synthetic: p53CDlac (v5)
source                     1..340
                           mol_type = protein
                           organism = synthetic construct
SEQUENCE: 10
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT VVRRCPHHER  180
CSDSDGLAPP QHLIRVEGNL RVEYLDDRNT FRHSVVVPYE PPEVGSDCTT IHYNYMCNSS  240
CMGGMNRRPI LTIITLEDSS GNLLGRNSFE VRVCACPGRD RRTEEENLRK KGEPHHELPP  300
GSTKRALPNN TSSSPQPKKK PLDDSLMQLA RQVSRLESGQ                        340

SEQ ID NO: 11              moltype = AA  length = 338
FEATURE                    Location/Qualifiers
REGION                     1..338
                           note = Synthetic: p53CDlac (v6)
source                     1..338
                           mol_type = protein
                           organism = synthetic construct
SEQUENCE: 11
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT VVRRCPHHER  180
CSDSDGLAPP QHLIRVEGNL RVEYLDDRNT FRHSVVVPYE PPEVGSDCTT IHYNYMCNSS  240
CMGGMNRRPI LTIITLEDSS GNLLGRNSFE VRVCACPGRD RRTEEENLRK KGEPHHELPP  300
GSTKRALPNN TSSSPQPKKK PLDLMQLARQ VSRLESGQ                          338

SEQ ID NO: 12              moltype = AA  length = 336
FEATURE                    Location/Qualifiers
REGION                     1..336
                           note = Synthetic: p53CDlac (v7)
source                     1..336
                           mol_type = protein
                           organism = synthetic construct
SEQUENCE: 12
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT VVRRCPHHER  180
CSDSDGLAPP QHLIRVEGNL RVEYLDDRNT FRHSVVVPYE PPEVGSDCTT IHYNYMCNSS  240
CMGGMNRRPI LTIITLEDSS GNLLGRNSFE VRVCACPGRD RRTEEENLRK KGEPHHELPP  300
GSTKRALPNN TSSSPQPKKK PLDQLARQVS RLESGQ                            336

SEQ ID NO: 13              moltype = AA  length = 334
FEATURE                    Location/Qualifiers
REGION                     1..334
                           note = Synthetic: p53CDlac (v8)
source                     1..334
                           mol_type = protein
                           organism = synthetic construct
SEQUENCE: 13
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT VVRRCPHHER  180
CSDSDGLAPP QHLIRVEGNL RVEYLDDRNT FRHSVVVPYE PPEVGSDCTT IHYNYMCNSS  240
CMGGMNRRPI LTIITLEDSS GNLLGRNSFE VRVCACPGRD RRTEEENLRK KGEPHHELPP  300
GSTKRALPNN TSSSPQPKKK PLDARQVSRL ESGQ                              334

SEQ ID NO: 14              moltype = AA  length = 418
FEATURE                    Location/Qualifiers
REGION                     1..418
                           note = Synthetic: p63CDlac (v1)
source                     1..418
                           mol_type = protein
                           organism = synthetic construct
SEQUENCE: 14
MNFETSRCAT LQYCPDPYIQ RFVETPAHFS WKESYYRSTM SQSTQTNEFL SPEVFQHIWD   60
FLEQPICSVQ PIDLNFVDEP SEDGATNKIE ISMDCIRMQD SDLSDPMWPQ YTNLGLLNSM  120
DQQIQNGSSS TSPYNTDHAQ NSVTAPSPYA QPSSTFDALS PSPAIPSNTD YPGPHSFDVS  180
FQQSSTAKSA TWTYSTELKK LYCQIAKTCP IQIKVMTPPP QGAVIRAMPV YKKAEHVTEV  240
VKRCPNHELS REFNEGQIAP PSHLIRVEGN SHAQYVEDPI TGRQSVLVPY EPPQVGTEFT  300
TVLYNFMCNS SCVGGMNRRP ILIIVTLETR DGQVLGRRCF EARICACPGR DRKADEDSIR  360
KQQVSDSTKN GDGTKRPFRQ NTHGIQMTSI KKRTASPRAL ADSLMQLARQ VSRLESGQ    418

SEQ ID NO: 15              moltype = AA  length = 416
FEATURE                    Location/Qualifiers
```

```
REGION                          1..416
                                note = Synthetic: p63CD1ac (v2)
source                          1..416
                                mol_type = protein
                                organism = synthetic construct
SEQUENCE: 15
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRSPRALAD SLMQLARQVS RLESGQ       416

SEQ ID NO: 16                   moltype = AA  length = 414
FEATURE                         Location/Qualifiers
REGION                          1..414
                                note = Synthetic: p63CD1ac (v3)
source                          1..414
                                mol_type = protein
                                organism = synthetic construct
SEQUENCE: 16
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRRALADSL MQLARQVSRL ESGQ         414

SEQ ID NO: 17                   moltype = AA  length = 412
FEATURE                         Location/Qualifiers
REGION                          1..412
                                note = Synthetic: p63CD1ac (v4)
source                          1..412
                                mol_type = protein
                                organism = synthetic construct
SEQUENCE: 17
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRLADSLMQ LARQVSRLES GQ           412

SEQ ID NO: 18                   moltype = AA  length = 410
FEATURE                         Location/Qualifiers
REGION                          1..410
                                note = Synthetic: p63CD1ac (v5)
source                          1..410
                                mol_type = protein
                                organism = synthetic construct
SEQUENCE: 18
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRDSLMQLA RQVSRLESGQ              410

SEQ ID NO: 19                   moltype = AA  length = 408
FEATURE                         Location/Qualifiers
REGION                          1..408
                                note = Synthetic: p63CD1ac (v6)
source                          1..408
                                mol_type = protein
                                organism = synthetic construct
SEQUENCE: 19
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRLMQLARQ VSRLESGQ                408

SEQ ID NO: 20                   moltype = AA  length = 406
```

| FEATURE | Location/Qualifiers |
| --- | --- |
| REGION | 1..406 |
|  | note = Synthetic: p63CDlac (v7) |
| source | 1..406 |
|  | mol_type = protein |
|  | organism = synthetic construct |

```
SEQUENCE: 20
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRQLARQVS RLESGQ                 406
```

| SEQ ID NO: 21 | moltype = AA length = 404 |
| --- | --- |
| FEATURE | Location/Qualifiers |
| REGION | 1..404 |
|  | note = Synthetic: p63CDlac (v8) |
| source | 1..404 |
|  | mol_type = protein |
|  | organism = synthetic construct |

```
SEQUENCE: 21
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRARQVSRL ESGQ                   404
```

| SEQ ID NO: 22 | moltype = AA length = 369 |
| --- | --- |
| FEATURE | Location/Qualifiers |
| REGION | 1..369 |
|  | note = Synthetic: p73CDlac (v1) |
| source | 1..369 |
|  | mol_type = protein |
|  | organism = synthetic construct |

```
SEQUENCE: 22
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVTASPRA LADSLMQLAR   360
QVSRLESGQ                                                         369
```

| SEQ ID NO: 23 | moltype = AA length = 367 |
| --- | --- |
| FEATURE | Location/Qualifiers |
| REGION | 1..367 |
|  | note = Synthetic: p73CDlac (v2) |
| source | 1..367 |
|  | mol_type = protein |
|  | organism = synthetic construct |

```
SEQUENCE: 23
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVSPRALA DSLMQLARQV   360
SRLESGQ                                                           367
```

| SEQ ID NO: 24 | moltype = AA length = 365 |
| --- | --- |
| FEATURE | Location/Qualifiers |
| REGION | 1..365 |
|  | note = Synthetic: p73CDlac (v3) |
| source | 1..365 |
|  | mol_type = protein |
|  | organism = synthetic construct |

```
SEQUENCE: 24
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVRALADS LMQLARQVSR   360
LESGQ                                                             365
```

```
SEQ ID NO: 25           moltype = AA  length = 363
FEATURE                 Location/Qualifiers
REGION                  1..363
                        note = Synthetic: p73CDlac (v4)
source                  1..363
                        mol_type = protein
                        organism = synthetic construct
SEQUENCE: 25
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVLADSLM QLARQVSRLE   360
SGQ                                                                363

SEQ ID NO: 26           moltype = AA  length = 361
FEATURE                 Location/Qualifiers
REGION                  1..361
                        note = Synthetic: p73CDlac (v5)
source                  1..361
                        mol_type = protein
                        organism = synthetic construct
SEQUENCE: 26
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVDSLMQL ARQVSRLESG   360
Q                                                                  361

SEQ ID NO: 27           moltype = AA  length = 359
FEATURE                 Location/Qualifiers
REGION                  1..359
                        note = Synthetic: p73CDlac (v6)
source                  1..359
                        mol_type = protein
                        organism = synthetic construct
SEQUENCE: 27
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVLMQLAR QVSRLESGQ    359

SEQ ID NO: 28           moltype = AA  length = 357
FEATURE                 Location/Qualifiers
REGION                  1..357
                        note = Synthetic: p73CDlac (v7)
source                  1..357
                        mol_type = protein
                        organism = synthetic construct
SEQUENCE: 28
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVQLARQV SRLESGQ      357

SEQ ID NO: 29           moltype = AA  length = 355
FEATURE                 Location/Qualifiers
REGION                  1..355
                        note = Synthetic: p73CDlac (v8)
source                  1..355
                        mol_type = protein
                        organism = synthetic construct
SEQUENCE: 29
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVARQVSR LESGQ        355

SEQ ID NO: 30           moltype = AA  length = 150
FEATURE                 Location/Qualifiers
```

```
REGION                          1..150
                                note = Synthetic: MatP
source                          1..150
                                mol_type = protein
                                organism = synthetic construct
SEQUENCE: 30
MKYQQLENLE SGWKWKYLVK KHREGELITR YIEASAAQEA VDVLLSLENE PVLVNGWIDK    60
HMNPELVNRM KQTIRARRKR HFNAEHQHTR KKSIDLEFIV WQRLAGLAQR RGKTLSETIV   120
QLIEDAENKE KYANKMSSLK QDLQALLGKE                                    150

SEQ ID NO: 31                   moltype = AA   length = 341
FEATURE                         Location/Qualifiers
REGION                          1..341
                                note = Synthetic: p53CDmat
source                          1..341
                                mol_type = protein
                                organism = synthetic construct
SEQUENCE: 31
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT VVRRCPHHER   180
CSDSDGLAPP QHLIRVEGNL RVEYLDDRNT FRHSVVVPYE PPEVGSDCTT IHYNYMCNSS   240
CMGGMNRRPI LTIITLEDSS GNLLGRNSFE VRVCACPGRD RRTEEENLRK KGEPHHELPP   300
GSTKRALPNN TSSSPQPKKK PLDANKMSSL KQDLQALLGK E                       341

SEQ ID NO: 32                   moltype = AA   length = 411
FEATURE                         Location/Qualifiers
REGION                          1..411
                                note = Synthetic: p63CDmat
source                          1..411
                                mol_type = protein
                                organism = synthetic construct
SEQUENCE: 32
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRANKMSSL KQDLQALLGK E            411

SEQ ID NO: 33                   moltype = AA   length = 362
FEATURE                         Location/Qualifiers
REGION                          1..362
                                note = Synthetic: p73CDmat
source                          1..362
                                mol_type = protein
                                organism = synthetic construct
SEQUENCE: 33
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVANKMSS LKQDLQALLG   360
KE                                                                  362

SEQ ID NO: 34                   moltype = AA   length = 853
FEATURE                         Location/Qualifiers
REGION                          1..853
                                note = Synthetic: MutS
source                          1..853
                                mol_type = protein
                                organism = synthetic construct
SEQUENCE: 34
MSAIENFDAH TPMMQQYLRL KAQHPEILLF YRMGDFYELF YDDAKRASQL LDISLTKRGA    60
SAGEPIPMAG IPYHAVENYL AKLVNQGESV AICEQIGDPA TSKGPVERKV VRIVTPGTIS   120
DEALLQERQD NLLAAIWQDS KGFGYATLDI SSGRFRLSEP ADRETMAAEL QRTNPAELLY   180
AEDFAEMSLI EGRRGLRRRP LWEFEIDTAR QQLNLQFGTR DLVGFGVENA PRGLCAAGCL   240
LQYAKDTQRT TLPHIRSITM EREQDSIIMD AATRRNLEIT QNLAGGAENT LASVLDCTVT   300
PMGSRMLKRW LHMPVRDTRV LLERQQTIGA LQDFTAGLQP VLRQVGDLER ILARLALRTA   360
RPRDLARMRH AFQQLPELRA QLETVDSAPV QALREKMGEF AELRDLLERA IIDTPPVLVR   420
DGGVIASGYN EELDEWRALA DGATDYLERL EVRERERTGL DTLKVGFNAV HGYYIQISRG   480
QSHLAPINYM RRQTLKNAER YIIPELKEYE DKVLTSKGKA LALEKQLYEE LFDLLLLPHLE   540
ALQQSASALA ELDVLVNLAE RAYTLNYTCP TFIDKPGIRI TEGRHPVVEQ VLNEPFIANP   600
LNLSPQRRML IITGPNMGGK STYMRQTALI ALMAYIGSYV PAQKVEIGPI DRIFTRVGAA   660
DDLASGRSTF MVEMTETANI LHNATEYSLV LMDEIGRGTS TYDGLSLAWA CAENLANKIK   720
ALTLFATHYF ELTQLPEKME GVANVHLDAL EHGDTIAFMH SVQDGAASKS YGLAVAALAG   780
VPKEVIKRAR QKLRELESIS PNAATQVDG TQMSLLSVPE ETSPAVEALE NLDPDSLTPR   840
```

QALEWIYRLK SLV                                                                  853

```
SEQ ID NO: 35           moltype = AA  length = 376
FEATURE                 Location/Qualifiers
REGION                  1..376
                        note = Synthetic: p53CDmut
source                  1..376
                        mol_type = protein
                        organism = synthetic construct
SEQUENCE: 35
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT VVRRCPHHER  180
CSDSDGLAPP QHLIRVEGNL RVEYLDDRNT FRHSVVVPYE PPEVGSDCTT IHYNYMCNSS  240
CMGGMNRRPI LTIITLEDSS GNLLGRNSFE VRVCACPGRD RRTEEENLRK KGEPHHELPP  300
GSTKRALPNN TSSSPQPKKK PLDPNAAATQ VDGTQMSLLS VPEETSPAVE ALENLDPDSL  360
TPRQALEWIY RLKSLV                                                  376

SEQ ID NO: 36           moltype = AA  length = 446
FEATURE                 Location/Qualifiers
REGION                  1..446
                        note = Synthetic: p63CDmut
source                  1..446
                        mol_type = protein
                        organism = synthetic construct
SEQUENCE: 36
MNFETSRCAT LQYCPDPYIQ RFVETPAHFS WKESYYRSTM SQSTQTNEFL SPEVFQHIWD   60
FLEQPICSVQ PIDLNFVDEP SEDGATNKIE ISMDCIRMQD SDLSDPMWPQ YTNLGLLNSM  120
DQQIQNGSSS TSPYNTDHAQ NSVTAPSPYA QPSSTFDALS PSPAIPSNTD YPGPHSFDVS  180
FQQSSTAKSA TWTYSTELKK LYCQIAKTCP IQIKVMTPPP QGAVIRAMPV YKKAEHVTEV  240
VKRCPNHELS REFNEGQIAP PSHLIRVEGN SHAQYVEDPI TGRQSVLVPY EPPQVGTEFT  300
TVLYNFMCNS SCVGGMNRRP ILIIVTLETR DGQVLGRRCF EARICACPGR DRKADEDSIR  360
KQQVSDSTKN GDGTKRPFRQ NTHGIQMTSI KKRPNAAATQ VDGTQMSLLS VPEETSPAVE  420
ALENLDPDSL TPRQALEWIY RLKSLV                                       446

SEQ ID NO: 37           moltype = AA  length = 397
FEATURE                 Location/Qualifiers
REGION                  1..397
                        note = Synthetic: p73CDmut
source                  1..397
                        mol_type = protein
                        organism = synthetic construct
SEQUENCE: 37
MAQSTATSPD GGTTFEHLWS SLEPDSTYFD LPQSSRGNNE VVGGTDSSMD VFHLEGMTTS   60
VMAQFNLLSS TMDQMSSRAA SASPYTPEHA ASVPTHSPYA QPSSTFDTMS PAPVIPSNTD  120
YPGPHHFEVT FQQSSTAKSA TWTYSPLLKK LYCQIAKTCP IQIKVSTPPP PGTAIRAMPV  180
YKKAEHVTDV VKRCPNHELG RDFNEGQSAP ASHLIRVEGN NLSQYVDDPV TGRQSVVVPY  240
EPPQVGTEFT TILYNFMCNS SCVGGMNRRP ILIIITLEMR DGQVLGRRSF EGRICACPGR  300
DRKADEDHYR EQQALNESSA KNGAASKRAF KQSPPAVPAL GAGVPNAAAT QVDGTQMSLL  360
SVPEETSPAV EALENLDPDS LTPRQALEWI YRLKSLV                           397

SEQ ID NO: 38           moltype = AA  length = 127
FEATURE                 Location/Qualifiers
REGION                  1..127
                        note = Synthetic: traM
source                  1..127
                        mol_type = protein
                        organism = synthetic construct
SEQUENCE: 38
MAKVNLYISN DAYEKINAII EKRRQEGARE KDVSFSATAS MLLELGLRVH EAQMERKESA   60
FNQTEFNKLL LECVVKTQSS VAKILGIESL SPHVSGNSKF EYANMVEDIR EKVSSEMERF  120
FPKNDDE                                                            127

SEQ ID NO: 39           moltype = AA  length = 350
FEATURE                 Location/Qualifiers
REGION                  1..350
                        note = Synthetic: p53CDtra
source                  1..350
                        mol_type = protein
                        organism = synthetic construct
SEQUENCE: 39
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT VVRRCPHHER  180
CSDSDGLAPP QHLIRVEGNL RVEYLDDRNT FRHSVVVPYE PPEVGSDCTT IHYNYMCNSS  240
CMGGMNRRPI LTIITLEDSS GNLLGRNSFE VRVCACPGRD RRTEEENLRK KGEPHHELPP  300
GSTKRALPNN TSSSPQPKKK PLDQTEFNKL LLECVVKTQS SVAKILGIES            350

SEQ ID NO: 40           moltype = AA  length = 420
```

```
FEATURE                 Location/Qualifiers
REGION                  1..420
                        note = Synthetic: p63CDtra
source                  1..420
                        mol_type = protein
                        organism = synthetic construct
SEQUENCE: 40
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRQTEFNKL LLECVVKTQS SVAKILGIES   420

SEQ ID NO: 41           moltype = AA  length = 371
FEATURE                 Location/Qualifiers
REGION                  1..371
                        note = Synthetic: p73CDtra
source                  1..371
                        mol_type = protein
                        organism = synthetic construct
SEQUENCE: 41
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVQTEFNK LLLECVVKTQ   360
SSVAKILGIE S                                                      371

SEQ ID NO: 42           moltype = AA  length = 321
FEATURE                 Location/Qualifiers
REGION                  1..321
                        note = Synthetic: GntR
source                  1..321
                        mol_type = protein
                        organism = synthetic construct
SEQUENCE: 42
MKKKRPVLQD VADRVGVTKM TVSRFLRNPE QVSVALRGKI AAALDELGYI PNRAPDILSN    60
ATSRAIGVLL PSLTNQVFAE VLRGIESVTD AHGYQTMLAH YGKPEMEQE RLESMLSWNI   120
DGLILTERTH TPRTLKMIEV AGIPVVELMD SKSPCLDIAV GFDNFEARQ MTTAIIARGH   180
RHIAYLGARL DERTIIKQKG YEQAMLDAGL VPYSVMVEQS SSYSSGIELI RQARREYPQL   240
DGVFCTNDDL AVGAAFECQR LGLKVPDDMA IAGFHGHDIG QVMEPRLASV GAERLLARIR   300
GESVTPKMLD LGFTLSPGGS I                                            321

SEQ ID NO: 43           moltype = AA  length = 344
FEATURE                 Location/Qualifiers
REGION                  1..344
                        note = Synthetic: p53CDgnt
source                  1..344
                        mol_type = protein
                        organism = synthetic construct
SEQUENCE: 43
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT VVRRCPHHER   180
CSDSDGLAPP QHLIRVEGNL RVEYLDDRNT FRHSVVVPYE PPEVGSDCTT IHYNYMCNSS   240
CMGGMNRRPI LTIITLEDSS GNLLGRNSFE VRVCACPGRD RRTEEENLRK KGEPHHELPP   300
GSTKRALPNN TSSSPQPKKK PLDGESVTPK MLDLGFTLSP GGSI                   344

SEQ ID NO: 44           moltype = AA  length = 414
FEATURE                 Location/Qualifiers
REGION                  1..414
                        note = Synthetic: p63CDgnt
source                  1..414
                        mol_type = protein
                        organism = synthetic construct
SEQUENCE: 44
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRGESVTPK MLDLGFTLSP GGSI         414

SEQ ID NO: 45           moltype = AA  length = 365
FEATURE                 Location/Qualifiers
```

```
REGION                      1..365
                            note = Synthetic: p73CDgnt
source                      1..365
                            mol_type = protein
                            organism = synthetic construct
SEQUENCE: 45
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTGN IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVGESVTP KMLDLGFTLS   360
PGGSI                                                               365

SEQ ID NO: 46               moltype = AA   length = 356
FEATURE                     Location/Qualifiers
REGION                      1..356
                            note = Synthetic: Lambda integrase
source                      1..356
                            mol_type = protein
                            organism = synthetic construct
SEQUENCE: 46
MGRRRSHERR DLPPNLYIRN NGYYCYRDPR TGKEFGLGRD RRIAITEAIQ ANIELFSGHK    60
HKPLTARINS DNSVTLHSWL DRYEKILASR GIKQKTLINY MSKIKAIRRG LPDAPLEDIT   120
TKEIAAMLNG YIDEGKAASA KLIRSTLSDA FREAIAEGHI TTNHVAATRA AKSEVRRSRL   180
TADEYLKIYQ AAESSPCWLR LAMELAVVTG QRVGDLCEMK WSDIVDGYLY VEQSKTGVKI   240
AIPTALHIDA LGISMKETLD KCKEILGGET IIASTRREPL SSGTVSRYFM RARKASGLSF   300
EGDPPTFHEL RSLSARLYEK QISDKFAQHL LGHKSDTMAS QYRDDRGREW DKIEIK       356

SEQ ID NO: 47               moltype = AA   length = 396
FEATURE                     Location/Qualifiers
REGION                      1..396
                            note = Synthetic: p53CDint
source                      1..396
                            mol_type = protein
                            organism = synthetic construct
SEQUENCE: 47
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT VVRRCPHHER   180
CSDSDGLAPP QHLIRVEGNL RVEYLDDRNT FRHSVVVPYE PPEVGSDCTT IHYNYMCNSS   240
CMGGMNRRPI LTIITLEDSS GNLLGRNSFE VRVCACPGRD RRTEEENLRK KGEPHHELPP   300
GSTKRALPNN TSSSPQPKKK PLDMGRRRSH ERRDLPPNLY IRNNGYYCYR DPRTGKEFGL   360
GRDRRIAITE AIQANIELFS GHKHKPLTAR INSDNS                             396

SEQ ID NO: 48               moltype = AA   length = 466
FEATURE                     Location/Qualifiers
REGION                      1..466
                            note = Synthetic: p63CDint
source                      1..466
                            mol_type = protein
                            organism = synthetic construct
SEQUENCE: 48
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRMGRRRSH ERRDLPPNLY IRNNGYYCYR   420
DPRTGKEFGL GRDRRIAITE AIQANIELFS GHKHKPLTAR INSDNS                  466

SEQ ID NO: 49               moltype = AA   length = 417
FEATURE                     Location/Qualifiers
REGION                      1..417
                            note = Synthetic: p73CDint
source                      1..417
                            mol_type = protein
                            organism = synthetic construct
SEQUENCE: 49
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTGN IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVMGRRRS HERRDLPPNL   360
YIRNNGYYCY RDPRTGKEFG LGRDRRIAIT EAIQANIELF SGHKHKPLTA RINSDNS      417

SEQ ID NO: 50               moltype = AA   length = 507
```

```
FEATURE               Location/Qualifiers
REGION                1..507
                      note = Measles virus phosphoprotein
source                1..507
                      mol_type = protein
                      organism = unidentified
SEQUENCE: 50
MAEEQARHVK NGLECIRALK AEPIGSLAIE EAMAAWSEIS DNPGQERATC KEEKAGSSGL  60
SKPCLSAIGS TEGGAPRIRG QGSGESDDDA ETLGTPSGNL QASSAGLQRY YVYDHSGEAV  120
KGIQDADSIV VQSGLDGDST LSGGDNESEN SDVDIGEPDT EGYAITDRGF APISMGFRAS  180
DVETAEGGEI HELLRLQSRG NNFLKSGKTL NVPPPPDPGR ANTSETPIKK GTDARLASFG  240
TEIASLLTGG ATQCARKSPS EPSGLGAPAG NVPECVSNAA LIQEWTPESG TTISPRSQNN  300
EEGGDYYDDE LFSDVQDIKT ALAKIHEDNQ KIISKLESLL LLKGEVESIK KQINKQNISI  360
STLEGHLSSI MIAIPGFGKD PNDPTADVEI NPDLKPIISR DSGRALAEVL KKPVASRQLQ  420
GMTSGRTSSR GQLLKEFQLK PIGKKMSSAV GFVPDTGPAS RSVIRSIIKS SRLEEDRKRY  480
LMTLLDDIKG ANDLAKFHQM LMKIIMK                                      507

SEQ ID NO: 51         moltype = AA  length = 387
FEATURE               Location/Qualifiers
REGION                1..387
                      note = Synthetic: p53CDmea
source                1..387
                      mol_type = protein
                      organism = synthetic construct
SEQUENCE: 51
MEEPQSDPSV EPPLSQETFS DLWKLLPENN VLSPLPSQAM DDLMLSPDDI EQWFTEDPGP  60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT VVRRCPHHER  180
CSDSDGLAPP QHLIRVEGNL RVEYLDDRNT FRHSVVVPYE PPEVGSDCTT IHYNYMCNSS  240
CMGGMNRRPI LTIITLEDSS GNLLGRNSFE VRVCACPGRD RRTEEENLRK KGEPHHELPP  300
GSTKRALPNN TSSSPQPKKK PLDDDELFSD VQDIKTALAK IHEDNQKIIS KLESLLLLKG  360
EVESIKKQIN KQNISISTLE GHLSSIM                                      387

SEQ ID NO: 52         moltype = AA  length = 457
FEATURE               Location/Qualifiers
REGION                1..457
                      note = Synthetic: p63CDmea
source                1..457
                      mol_type = protein
                      organism = synthetic construct
SEQUENCE: 52
MNFETSRCAT LQYCPDPYIQ RFVETPAHFS WKESYYRSTM SQSTQTNEFL SPEVFQHIWD  60
FLEQPICSVQ PIDLNFVDEP SEDGATNKIE ISMDCIRMQD SDLSDPMWPQ YTNLGLLNSM  120
DQQIQNGSSS TSPYNTDHAQ NSVTAPSPYA QPSSTFDALS PSPAIPSNTD YPGPHSFDVS  180
FQQSSTAKSA TWTYSTELKK LYCQIAKTCP IQIKVMTPPP QGAVIRAMPV YKKAEHVTEV  240
VKRCPNHELS REFNEGQIAP PSHLIRVEGN SHAQYVEDPI TGRQSVLVPY EPPQVGTEFT  300
TVLYNFMCNS SCVGGMNRRP ILIIVTLETR DGQVLGRRCF EARICACPGR DRKADEDSIR  360
KQQVSDSTKN GDGTKRPFRQ NTHGIQMTSI KKRDDELFSD VQDIKTALAK IHEDNQKIIS  420
KLESLLLLKG EVESIKKQIN KQNISISTLE GHLSSIM                           457

SEQ ID NO: 53         moltype = AA  length = 408
FEATURE               Location/Qualifiers
REGION                1..408
                      note = Synthetic: p73CDmea
source                1..408
                      mol_type = protein
                      organism = synthetic construct
SEQUENCE: 53
MAQSTATSPD GGTTFEHLWS SLEPDSTYFD LPQSSRGNNE VVGGTDSSMD VFHLEGMTTS  60
VMAQFNLLSS TMDQMSSRAA SASPYTPEHA ASVPTHSPYA QPSSTFDTMS PAPVIPSNTD  120
YPGPHHFEVT FQQSSTAKSA TWTYSPLLKK LYCQIAKTCP IQIKVSTPPP PGTAIRAMPV  180
YKKAEHVTDV VKRCPNHELG RDFNEGQSAP ASHLIRVEGN NLSQYVDDPV TGRQSVVVPY  240
EPPQVGTEFT TILYNFMCNS SCVGGMNRRP ILIIITLEMR DGQVLGRRSF EGRICACPGR  300
DRKADEDHYR EQQALNESSA KNGAASKRAF KQSPPAVPAL GAGVDDELFS DVQDIKTALA  360
KIHEDNQKII SKLESLLLLK GEVESIKKQI NKQNISISTL EGHLSSIM               408

SEQ ID NO: 54         moltype = AA  length = 709
FEATURE               Location/Qualifiers
REGION                1..709
                      note = Nipah viral phosphoprotein
source                1..709
                      mol_type = protein
                      organism = unidentified
SEQUENCE: 54
MDKLELVNDG LNIIDFIQKN QKEIQKTYGR SSIQQPSIKD QTKAWEDFLQ CTSGESEQVE  60
GGMSKDDGDV ERRNLEDLSS TSPTDGTIGK RVSNTRDWAE GSDDIQLDPV VTDVVYHDHG  120
GECTGYGFTS SPERGWSDYT SGANNGNVCL VSDAKMLSYA PEIAVSKEDR ETDLVHLENK  180
LSTTGLNPTA VPFTLRNLSD PAKDSPVIAE HYYGLGVKEQ NVGPQTSRNV NLDSIKLYTS  240
DDEEADQLEF EDEFAGSSSE VIVGISPEDE EPSSVGGKPN ESIGRTIEGQ SIRDNLQAKD  300
```

```
NKSTDVPGAG PKDSAVKEEP PQKRLPMLAE EFECSGSEDP IIRELLKENS LINCQQGKDA    360
QPPYHWSIER SISPDKTEIV NGAVQTADRQ RPGTPMPKSR GIPIKKGTDA KYPSAGTENV    420
PGSKSGATRH VRGSPPYQEG KSVNAENVQL NASTAVKETD KSEVNPVDDN DSLDDKYIMP    480
SDDFSNTFFP HDTDRLNYHA DHLGDYDLET LCEESVLMGV INSIKLINLD MRLNHIEEQV    540
KEIPKIINKL ESIDRVLAKT NTALSTIEGH LVSMMIMIPG KGKGERKGKN NPELKPVIGR    600
DILEQQSLFS FDNVKNFRDG SLTNEPYGAA VQLREDLILP ELNFEETNAS QFVPMADDSS    660
RDVIKTLIRT HIKDRELRSE LIGYLNKAEN DEEIQEIANT VNDIIDGNI               709

SEQ ID NO: 55           moltype = AA  length = 402
FEATURE                 Location/Qualifiers
REGION                  1..402
                        note = Synthetic: p53CDnip
source                  1..402
                        mol_type = protein
                        organism = synthetic construct
SEQUENCE: 55
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK    120
SVTCTYSPAL NKMFCQLAKT CPVQLWVDST PPPGTRVRAM AIYKQSQHMT VVRRCPHHER    180
CSDSDGLAPP QHLIRVEGNL RVEYLDDRNT FRHSVVVPYE PPEVGSDCTT IHYNYMCNSS    240
CMGGMNRRPI LTIITLEDSS GNLLGRNSFE VRVCACPGRD RRTEEENLRK KGEPHHELPP    300
GSTKRALPNN TSSSPQPKKK PLDYHADHLG DYDLETLCEE SVLMGVINSI KLINLDMRLN    360
HIEEQVKEIP KIINKLESID RVLAKTNTAL STIEGHLVSM MI                      402

SEQ ID NO: 56           moltype = AA  length = 472
FEATURE                 Location/Qualifiers
REGION                  1..472
                        note = Synthetic: p63CDnip
source                  1..472
                        mol_type = protein
                        organism = synthetic construct
SEQUENCE: 56
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM    120
DQQIQNGSSS TSPYNTDHAQ NSVTAPSPYA QPSSTFDALS PSPAIPSNTD YPGPHSFDVS    180
FQQSSTAKSA TWTYSTELKK LYCQIAKTCP IQIKVMTPPP QGAVIRAMPV YKKAEHVTEV    240
VKRCPNHELS REFNEGQIAP PSHLIRVEGN SHAQYVEDPI TGRQSVLVPY EPPQVGTEFT    300
TVLYNFMCNS SCVGGMNRRP ILIIVTLETR DGQVLGRRCF EARICACPGR DRKADEDSIR    360
KQQVSDSTKN GDGTKRPFRQ NTHGIQMTSI KKRYHADHLG DYDLETLCEE SVLMGVINSI    420
KLINLDMRLN HIEEQVKEIP KIINKLESID RVLAKTNTAL STIEGHLVSM MI            472

SEQ ID NO: 57           moltype = AA  length = 423
FEATURE                 Location/Qualifiers
REGION                  1..423
                        note = Synthetic: p73CDnip
source                  1..423
                        mol_type = protein
                        organism = synthetic construct
SEQUENCE: 57
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD    120
YPGPHHFEVT FQQSSTAKSA TWTYSPLLKK LYCQIAKTCP IQIKVSTPPP PGTAIRAMPV    180
YKKAEHVTDV VKRCPNHELG RDFNEGQSAP ASHLIRVEGN NLSQYVDDPV TGRQSVVVPY    240
EPPQVGTEFT TILYNFMCNS SCVGGMNRRP ILIIITLEMR DGQVLGRRSF EGRICACPGR    300
DRKADEDHYR EQQALNESSA KNGAASKRAF KQSPPAVPAL GAGVYHADHL GDYDLETLCE    360
ESVLMGVINS IKLINLDMRL NHIEEQVKEI PKIINKLESI DRVLAKTNTA LSTIEGHLVS    420
MMI                                                                 423

SEQ ID NO: 58           moltype = AA  length = 254
FEATURE                 Location/Qualifiers
REGION                  1..254
                        note = Tapeworm VASP
source                  1..254
                        mol_type = protein
                        organism = unidentified
SEQUENCE: 58
PPPPPPPPPP PPPPPSQSAS ASSLQSMNNE HKASTASALS DLPHDLHAAY PNDTDVGSSG    60
GGGGWLATQL RLAKQQRMQR QQTATGVGDS TSASGGQTGI PGGTGTLSRA VGADMMSDLQ    120
RVLAARRRAR EGDTDETGDG ATATGVAACN DTNYSTTGHY RRPSQSSNPS NHNNNSTTAT    180
YATPVAPSQT PSAYGTIRKN STSVISSDSS GTQTITRADL ETFKREILAE FRKEVKSLKS    240
EILDALRVSN NRLS                                                     254

SEQ ID NO: 59           moltype = AA  length = 353
FEATURE                 Location/Qualifiers
REGION                  1..353
                        note = Synthetic: p53CDvasp
source                  1..353
                        mol_type = protein
                        organism = synthetic construct
```

```
SEQUENCE: 59
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT VVRRCPHHER   180
CSDSDGLAPP QHLIRVEGNL RVEYLDDRNT FRHSVVVPYE PPEVGSDCTT IHYNYMCNSS   240
CMGGMNRRPI LTIITLEDSS GNLLGRNSFE VRVCACPGRD RRTEEENLRK KGEPHHELPP   300
GSTKRALPNN TSSSPQPKKK PLDADLETFK REILAEFRKE VKSLKSEILD ALR          353

SEQ ID NO: 60            moltype = AA   length = 423
FEATURE                  Location/Qualifiers
REGION                   1..423
                         note = Synthetic: p63CDvasp
source                   1..423
                         mol_type = protein
                         organism = synthetic construct SEQUENCE: 60
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRADLETFK REILAEFRKE VKSLKSEILD   420
ALR                                                                 423

SEQ ID NO: 61            moltype = AA   length = 374
FEATURE                  Location/Qualifiers
REGION                   1..374
                         note = Synthetic: p73CDvasp
source                   1..374
                         mol_type = protein
                         organism = synthetic construct SEQUENCE: 61
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVADLETF KREILAEFRK   360
EVKSLKSEIL DALR                                                     374

SEQ ID NO: 62            moltype = AA   length = 631
FEATURE                  Location/Qualifiers
REGION                   1..631
                         note = Chicken KCNA5
source                   1..631
                         mol_type = protein
                         organism = unidentified SEQUENCE: 62
MEIALVTLEN GGGGAISSVE YATAGSTSGS TRARRQSELL HTAGSTFVPR LSDGKEGTPP    60
PSPPPQVDEE RERLPPTRG GGGRRCSSSE GSINGRAASG PQPQPHAPRS GPAAEMDPPE   120
EGGHRQGMTM AAAGDEEGMK AASRSAMHHQ RVLINISGLH FETQLGTLNQ FPDTLLGDPD   180
KRMRYFDPLR NEYFFDRNRP SFDGILYFYQ SGGKLRRPVN VSIDVFADEI RFYQLGKEAM   240
ERFQEDEGFI REQEKPLPHS EFQRQVWLIF EYPESSSSAR AIAIVSVLVI LISIITFCLE   300
TLPEFRDERE IPMSLPPQSG GLNATAGDSP PMQSPSSISD PFFIIETTCV IWFTFELLVR   360
FFTCPSKPEF SRNIMNIIDI VAIIPYFITL GTELAHEQQQ PGGSSNNGSG SQQQAMSLAI   420
LRVIRLVRVF RIFKLSRHSK GLQILGQTLK ASMRELGLLI FFLFIGVILF SSAAYFAEAD   480
DPESHFSSIP DAFWWAVVTM TTVGYGDMRP ITVGGKIVGS LCAIAGVLTI ALPVPVIVSN   540
FNYFYHRETD HEEQAMLKEE HSSAQSSITG VDGKRRSSKN SLNKSVVHLE NNEGFKSASP   600
LEKTNIKAKS NVDLRKSLYA LCLDSSRETD L                                  631

SEQ ID NO: 63            moltype = AA   length = 370
FEATURE                  Location/Qualifiers
REGION                   1..370
                         note = Synthetic: p53CDkcna5
source                   1..370
                         mol_type = protein
                         organism = synthetic construct SEQUENCE: 63
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT VVRRCPHHER   180
CSDSDGLAPP QHLIRVEGNL RVEYLDDRNT FRHSVVVPYE PPEVGSDCTT IHYNYMCNSS   240
CMGGMNRRPI LTIITLEDSS GNLLGRNSFE VRVCACPGRD RRTEEENLRK KGEPHHELPP   300
GSTKRALPNN TSSSPQPKKK PLDDGILYFY QSGGKLRRPV NVSIDVFADE IRFYQLGKEA   360
MERFQEDEGF                                                          370

SEQ ID NO: 64            moltype = AA   length = 440
FEATURE                  Location/Qualifiers
```

```
REGION                      1..440
                            note = Synthetic: p63CDkcna5
source                      1..440
                            mol_type = protein
                            organism = synthetic construct
SEQUENCE: 64
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
TVLYNFMCNS SCVGGMNRRP ILIIVTLETR DGQVLGRRCF EARICACPGR DRKADEDSIR   360
KQQVSDSTKN GDGTKRPFRQ NTHGIQMTSI KKRDGILYFY QSGGKLRRPV NVSIDVFADE   420
IRFYQLGKEA MERFQEDEGF                                               440

SEQ ID NO: 65               moltype = AA   length = 391
FEATURE                     Location/Qualifiers
REGION                      1..391
                            note = Synthetic: p73CDkcna5
source                      1..391
                            mol_type = protein
                            organism = synthetic construct
SEQUENCE: 65
MAQSTATSPD GGTTFEHLWS SLEPDSTYFD LPQSSRGNNE VVGGTDSSMD VFHLEGMTTS    60
VMAQFNLLSS TMDQMSSRAA SASPYTPEHA ASVPTHSPYA QPSSTFDTMS PAPVIPSNTD   120
YPGPHHFEVT FQQSSTAKSA TWTYSPLLKK LYCQIAKTCP IQIKVSTPPP PGTAIRAMPV   180
YKKAEHVTDV VKRCPNHELG RDFNEGQSAP ASHLIRVEGN NLSQYVDDPV TGRQSVVVPY   240
EPPQVGTEFT TILYNFMCNS SCVGGMNRRP ILIIITLEMR DGQVLGRRSF EGRICACPGR   300
DRKADEDHYR EQQALNESSA KNGAASKRAF KQSPPAVPAL GAGVDGILYF YQSGGKLRRP   360
VNVSIDVFAD EIRFYQLGKE AMERFQEDEG F                                  391

SEQ ID NO: 66               moltype = AA   length = 602
FEATURE                     Location/Qualifiers
REGION                      1..602
                            note = Cat Cholinesterase
source                      1..602
                            mol_type = protein
                            organism = unidentified
SEQUENCE: 66
MQSKGTIISI QFLLRFLLLW VLIGKSHTEE DIIITTKNGK VRGMNLPVLD GTVTAFLGIP    60
YAQPPLGRLR FKKPQFLTKW SDIWNATKYA NSCYQNADQS FPGFPGSEMW NPNTDLSEDC   120
LYLNVWIPTP KPKNATVMIW IYGGGFQTGT SSLPVYDGLF LARVERVIVV SMNYRVGALG   180
FLALPGNPEV PGNMGLFDQQ LALQWVQKNI AAFGGNPKSV TLFGESAGAG SVSLHLLSPR   240
SQPLFTRAIL QSGSSNAPWA VMSLDEAKNR TLTLAKFIGC SKENDTEIIK CLRNKDPQEI   300
LLNELLVVPS DTLLSVNFGP VVDGDFLTDM PDTLLQLGQF KKTQILVGVN KDEGTAFLVY   360
GAPGFSKDND SIITRKEFQE GLKIYFPGVS EFGREAILFY YVDLLDDQRA EKYREALDDV   420
LGDYNIICPA LEFTTKFSEL GNNAFFYYFE HRSSQLPWPA TQNNSTRWPA FRSTDQKYLT   480
RVNYTRAEEI LSRSIMNYWA NFAKYGNPNG TQNNSTRWPA FRSTDQKYLT LNAESPKVYT   540
KLRAQQCRFW TLFFPKVLEM TGNIDEAERE WRAGFYRWNN YMMDWKNQFN DYTSKKESCA   600
GL                                                                  602

SEQ ID NO: 67               moltype = AA   length = 360
FEATURE                     Location/Qualifiers
REGION                      1..360
                            note = Synthetic: p53CDchol
source                      1..360
                            mol_type = protein
                            organism = synthetic construct
SEQUENCE: 67
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT VVRRCPHHER   180
CSDSDGLAPP QHLIRVEGNL RVEYLDDRNT FRHSVVVPYE PPEVGSDCTT IHYNYMCNSS   240
CMGGMNRRPI LTIITLEDSS GNLLGRNSFE VRVCACPGRD RRTEEENLRK KGEPHHELPP   300
GSTKRALPNN TSSSPQPKKK PLDDEAEREW RAGFYRWNNY MMDWKNQFND YTSKKESCAG   360

SEQ ID NO: 68               moltype = AA   length = 430
FEATURE                     Location/Qualifiers
REGION                      1..430
                            note = Synthetic: p63CDchol
source                      1..430
                            mol_type = protein
                            organism = synthetic construct
SEQUENCE: 68
MNFETSRCAT LQYCPDPYIQ RFVETPAHFS WKESYYRSTM SQSTQTNEFL SPEVFQHIWD    60
FLEQPICSVQ PIDLNFVDEP SEDGATNKIE ISMDCIRMQD SDLSDPMWPQ YTNLGLLNSM   120
DQQIQNGSSS TSPYNTDHAQ NSVTAPSPYA QPSSTFDALS PSPAIPSNTD YPGPHSFDVS   180
FQQSSTAKSA TWTYSTELKK LYCQIAKTCP IQIKVMTPPP QGAVIRAMPV YKKAEHVTEV   240
VKRCPNHELS REFNEGQIAP PSHLIRVEGN SHAQYVEDPI TGRQSVLVPY EPPQVGTEFT   300
```

```
TVLYNFMCNS  SCVGGMNRRP  ILIIVTLETR  DGQVLGRRCF  EARICACPGR  DRKADEDSIR   360
KQQVSDSTKN  GDGTKRPFRQ  NTHGIQMTSI  KKRDEAEREW  RAGFYRWNNY  MMDWKNQFND   420
YTSKKESCAG                                                              430

SEQ ID NO: 69           moltype = AA   length = 381
FEATURE                 Location/Qualifiers
REGION                  1..381
                        note = Synthetic: p73CDchol
source                  1..381
                        mol_type = protein
                        organism = synthetic construct
SEQUENCE: 69
MAQSTATSPD  GGTTFEHLWS  SLEPDSTYFD  LPQSSRGNNE  VVGGTDSSMD  VFHLEGMTTS    60
VMAQFNLLSS  TMDQMSSRAA  SASPYTPEHA  ASVPTHSPYA  QPSSTFDTMS  PAPVIPSNTD   120
YPGPHHFEVT  FQQSSTAKSA  TWTYSPLLKK  LYCQIAKTCP  IQIKVSTPPP  PGTAIRAMPV   180
YKKAEHVTDV  VKRCPNHELG  RDFNEGQSAP  ASHLIRVEGN  NLSQYVDDPV  TGRQSVVVPY   240
EPPQVGTEFT  TILYNFMCNS  SCVGGMNRRP  ILIIITLEMR  DGQVLGRRSF  EGRICACPGR   300
DRKADEDHYR  EQQALNESSA  KNGAASKRAF  KQSPPAVPAL  GAGVDEAERE  WRAGFYRWNN   360
YMMDWKNQFN  DYTSKKESCA  G                                               381
```